United States Patent
Kaneko

(10) Patent No.: US 12,383,215 B2
(45) Date of Patent: Aug. 12, 2025

(54) MEDICAL APPARATUS

(71) Applicant: FUJIFILM CORPORATION, Tokyo (JP)

(72) Inventor: Yasuhisa Kaneko, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 219 days.

(21) Appl. No.: 18/298,372

(22) Filed: Apr. 11, 2023

(65) Prior Publication Data
US 2023/0240631 A1 Aug. 3, 2023

Related U.S. Application Data

(63) Continuation of application No. PCT/JP2021/036240, filed on Sep. 30, 2021.

(30) Foreign Application Priority Data

Oct. 28, 2020 (JP) ................. 2020-180888

(51) Int. Cl.
*A61B 6/00* (2024.01)
*A61B 6/04* (2006.01)
(Continued)

(52) U.S. Cl.
CPC .......... *A61B 6/4423* (2013.01); *A61B 6/0421* (2013.01); *A61L 2/10* (2013.01);
(Continued)

(58) Field of Classification Search
CPC ..... A61B 6/4423; A61B 6/0421; A61B 6/037; A61B 6/487; A61B 6/0407; A61B 6/032;
(Continued)

(56) References Cited

U.S. PATENT DOCUMENTS

| | | | |
|---|---|---|---|
| 3,789,228 A * | 1/1974 | Bouchard | F24F 8/22 250/492.1 |
| 2012/0008741 A1 | 1/2012 | Hendriks et al. | |
| 2013/0052079 A1 | 2/2013 | Bernstein | |
| 2014/0341777 A1 | 11/2014 | Deshays et al. | |

FOREIGN PATENT DOCUMENTS

| | | |
|---|---|---|
| CN | 203208040 U | 9/2013 |
| CN | 112023087 A * | 12/2020 |

(Continued)

OTHER PUBLICATIONS

International Search Report issued in International Application No. PCT/JP2021/036240 on Dec. 21, 2021.
(Continued)

*Primary Examiner* — Kiho Kim
(74) *Attorney, Agent, or Firm* — SOLARIS Intellectual Property Group, PLLC

(57) ABSTRACT

A medical apparatus includes a table portion that has a contact surface with which a subject comes into contact, a structural portion in which a relative position with the table portion is determined within a predetermined range, and a sterilization unit that is attached to the table portion or the structural portion and sterilizes the contact surface. The sterilization unit is configured to switch between a first state in which the sterilization unit is in contact with or close to the contact surface and a second state in which the sterilization unit is separated from the contact surface.

15 Claims, 29 Drawing Sheets

(51) Int. Cl.
*A61L 2/10* (2006.01)
*A61L 2/18* (2006.01)
*A61L 2/24* (2006.01)
*A61L 2/26* (2006.01)

(52) U.S. Cl.
CPC .................. *A61L 2/18* (2013.01); *A61L 2/24* (2013.01); *A61L 2/26* (2013.01); *A61L 2202/11* (2013.01); *A61L 2202/14* (2013.01); *A61L 2202/24* (2013.01)

(58) Field of Classification Search
CPC ..... A61B 6/54; A61L 2/10; A61L 2/18; A61L 2/24; A61L 2/26; A61L 2202/11; A61L 2202/14; A61L 2202/24; A61L 2/088; A61L 2/22; A61L 2202/15; A61L 2/20
See application file for complete search history.

(56) References Cited

FOREIGN PATENT DOCUMENTS

| | | | |
|---|---|---|---|
| CN | 116269468 A | * | 6/2023 |
| JP | H05-212029 A | | 8/1993 |
| JP | H09-253083 A | | 9/1997 |
| JP | 2009-213557 A | | 9/2009 |
| JP | 2012-511381 A | | 5/2012 |

OTHER PUBLICATIONS

Written Opinion of the ISA issued in International Application No. PCT/JP2021/036240 on Dec. 21, 2021.
English language translation of the following: Office action dated Jun. 24, 2025, from the JPO in a Japanese patent application No. 2022-558943 corresponding to the instant patent application.

* cited by examiner

MEDICAL APPARATUS

CROSS-REFERENCE TO RELATED APPLICATIONS

This application is a continuation application of International Application No. PCT/JP2021/036240, filed Sep. 30, 2021, the disclosure of which is incorporated herein by reference in its entirety. Further, this application claims priority from Japanese Patent Application No. 2020-180888, filed on Oct. 28, 2020, the disclosure of which is incorporated herein by reference in its entirety.

BACKGROUND

1. Technical Field

The disclosed technology relates to a medical apparatus.

2. Description of the Related Art

There is a medical apparatus such as a diagnosis apparatus and a treatment apparatus that sterilizes a portion of an examination table or the like that comes into contact with a subject is known. For example, JP2012-511381A discloses that, in an X-ray apparatus, an illumination device mounted on a C-arm sterilizes an examination table by transmitting UV radiation.

SUMMARY

In a case where an examinee to be diagnosed or treated by a medical apparatus such as a diagnosis apparatus and a treatment apparatus is infected with a pathogen such as a bacterium or a virus, there is a risk that another examinee or a doctor will be infected with the pathogen via a portion of the medical apparatus with which the examinee comes into contact. Therefore, for example, it is preferable to increase the sterilization frequency such as sterilizing a portion of the medical apparatus with which the examinee comes into contact each time the treatment for one examinee has been completed.

JP2012-511381A discloses that the illumination device mounted on the C-arm sterilizes the examination table by emitting ultraviolet rays. However, in a case where a distance from a light source that emits ultraviolet rays to the examination table is long, the energy of the ultraviolet rays is diffused, and thus a sufficient bactericidal effect cannot be obtained. On the other hand, in a case where the distance from the light source that emits ultraviolet rays to the examination table is short, there is a possibility that the normal use (for example, X-ray imaging) of the medical apparatus may be hindered.

The disclosed technology has been made in view of the circumstances, and an object thereof is to perform, in a medical apparatus having a contact surface with which a subject comes into contact, effective sterilization of the contact surface without hindering normal use of the medical apparatus.

According to the disclosed technology, there is provided a medical apparatus including a table portion that has a contact surface with which a subject comes into contact; a structural portion in which a relative position with the table portion is determined within a predetermined range; and a sterilization unit that is attached to the table portion or the structural portion and sterilizes the contact surface, in which the sterilization unit is configured to switch between a first state in which the sterilization unit is in contact with or close to the contact surface and a second state in which the sterilization unit is separated from the contact surface.

It is preferable that in the first state, a distance between the sterilization unit and the contact surface may be 10 cm or less. The structural portion may be an examination unit that examines the subject in a non-contact manner. The structural portion may be a radiation source unit that emits radiation. The structural portion may be a detection unit that detects radiation. The sterilization unit may include a light source that emits ultraviolet rays.

The medical apparatus may further include a radiation source unit that emits radiation. In this case, the sterilization unit may include a phosphor that absorbs radiation and emits ultraviolet rays, and, in the first state, the radiation radiated from the radiation source unit may be applied to the phosphor.

The sterilization unit may eject a liquid or a gas having a bactericidal action toward the contact surface. The sterilization unit may include a wiping member that is a member impregnated with a liquid having a bactericidal action and wipes the contact surface.

The medical apparatus may further include a fixing unit that fixes the subject by sandwiching the subject between the table portion and the fixing unit. In this case, the sterilization unit may be configured to emit at least one of light, a liquid, or a gas having a bactericidal action from both a first surface and a second surface opposite to the first surface, and, in the first state, the first surface may face the contact surface of the table portion and the second surface may face a surface of the fixing unit that comes into contact with the subject.

The medical apparatus may further include a control unit that controls a sterilization process of sterilizing the contact surface with the sterilization unit. At least one of the sterilization unit or the contact surface may be movable in a surface direction of the contact surface. In this case, in the sterilization process, the control unit may set a state of the sterilization unit to the first state, and move at least one of the sterilization unit or the contact surface in the surface direction.

The medical apparatus may further include a region detection unit that detects a contact region of the contact surface with which the subject comes into contact. In this case, in the sterilization process, the control unit may sterilize the contact surface by setting a sterilization intensity in the contact region detected by the region detection unit to be higher than sterilization intensity in a region other than the contact region.

The medical apparatus may further include a height detection unit that detects a height of the contact surface. In this case, in the sterilization process, the control unit may control a height of the sterilization unit in accordance with a change in the height of the contact surface detected by the height detection unit such that a distance between the sterilization unit and the contact surface is constant.

The control unit may start the sterilization process on the basis of order information regarding diagnosis or treatment of the subject.

In the sterilization process, the control unit may sterilize the contact surface in a sterilization mode selected from a plurality of sterilization modes in which sterilization intensities are different from each other.

The table portion may be an examination table on which an examinee to be treated in the medical apparatus lies.

According to the disclosed technology, in a medical apparatus having a contact surface with which a subject comes into contact, it is possible to effectively sterilize the contact surface without hindering normal use of the medical apparatus.

BRIEF DESCRIPTION OF THE DRAWINGS

Exemplary embodiments according to the technique of the present disclosure will be described in detail based on the following figures, wherein.

DETAILED DESCRIPTION

Figure 1A:
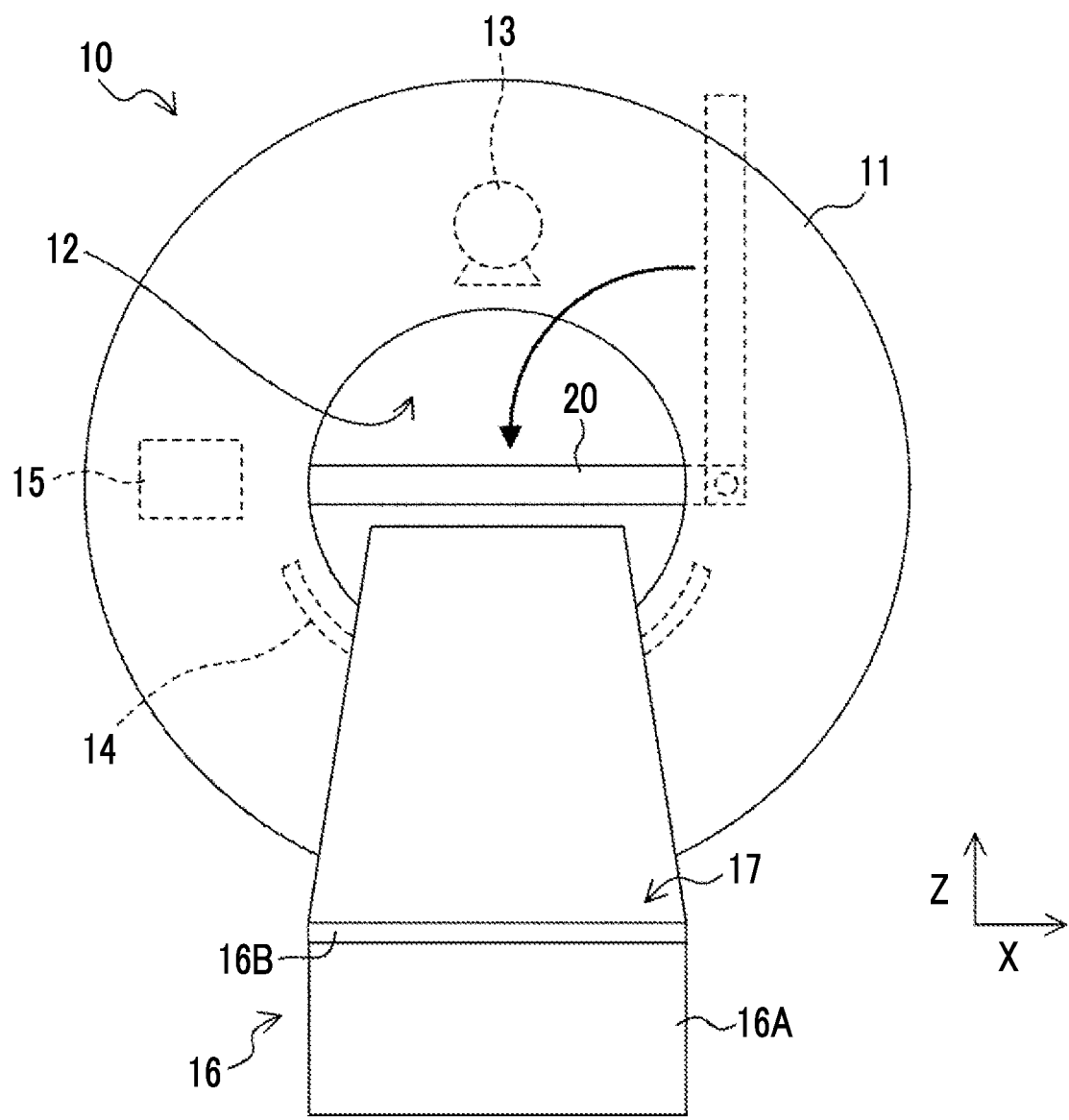
FIG. 1A is a diagram showing an example of a configuration of a CT apparatus that is an example of a medical apparatus according to an embodiment of the disclosed technology.

Hereinafter, an example of an embodiment of the disclosed technology will be described with reference to the drawings. In each drawing, the same or equivalent constituents and portions are given the same reference numerals, and redundant description will be omitted as appropriate.

First Embodiment

FIG. 1A is a diagram showing an example of a configuration of a CT apparatus 10 that is an example of a medical apparatus according to a first embodiment of the disclosed technology. The CT apparatus 10 according to the present embodiment includes a gantry 11 and an examination table 16. The gantry 11 has a tunnel-like structure having an opening portion 12 at the center thereof. A radiation source unit 13 that emits X-rays and a detection unit 14 that detects X-rays and generates a radiation image are provided inside the gantry 11. The radiation source unit 13 and the detection unit 14 can be each rotated along the annular shape of the gantry 11 while maintaining a positional relationship of facing each other. A control unit 15 that controls an operation of the CT apparatus 10 is provided inside the gantry 11.

The examination table 16 has a base portion 16A fixed to a floor and a bed portion 16B on which a subject (examinee) lies. A surface of the bed portion 16B is a contact surface 17 with which the subject (examinee) comes into contact. The bed portion 16B is slidable in a surface direction of the contact surface 17. In a case of capturing a radiation image, the bed portion 16B is slid to transport a subject (examinee) lying on the bed portion 16B into the opening portion 12 of the gantry 11.

The examination table 16 is an example of a "table portion" in the disclosed technology. The "table portion" has a contact surface with which a subject (examinee) comes into contact. The gantry 11 is an example of a "structural portion" in the disclosed technology, and is also an example of an "examination unit". The "structural portion" is defined as a relative position with respect to the "table portion" within a predetermined range. The "examination unit" examines a subject (examinee) in a non-contact manner. In the following description, a vertical direction will be referred to as a Z direction, a slide direction of the bed portion 16B will be referred to as a Y direction, and a direction perpendicular to both the Z direction and the Y direction will be referred to as an X direction.

Figure 1B:
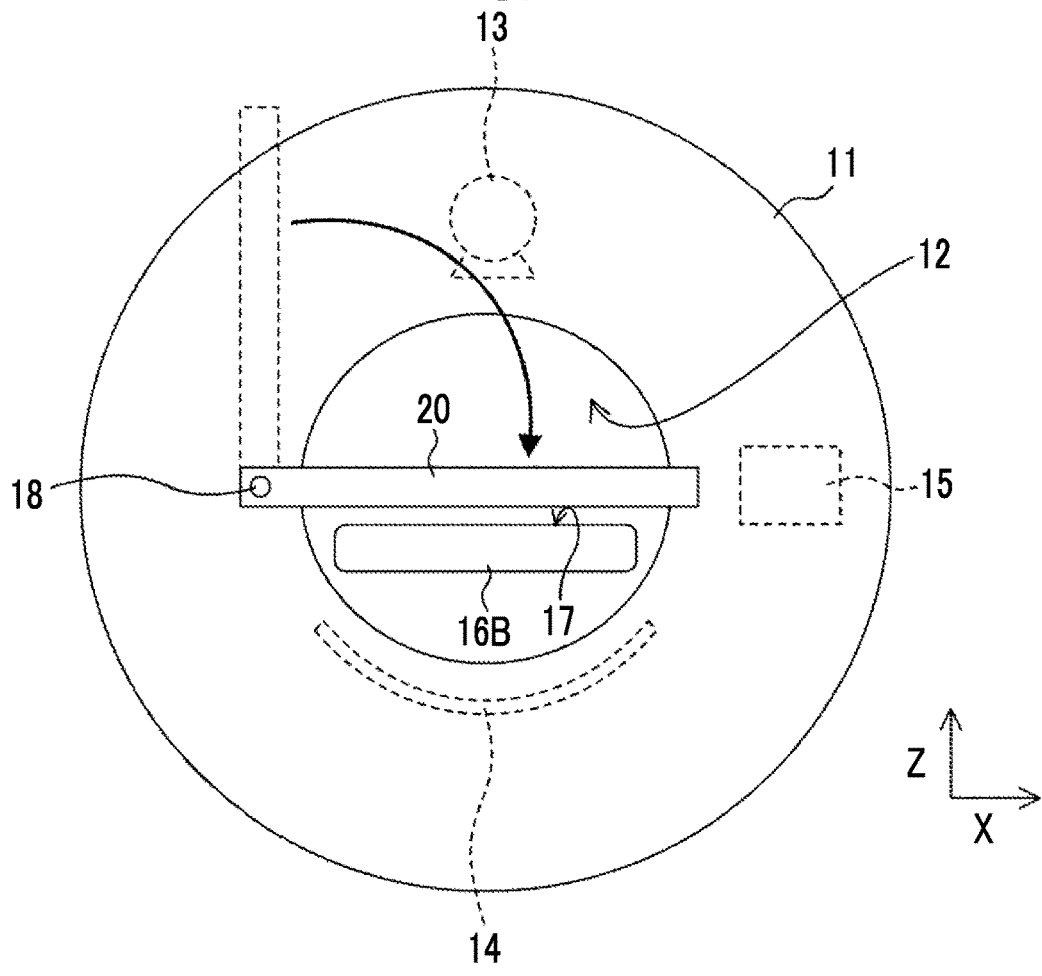
FIG. 1B is a view of the CT apparatus according to the embodiment of the disclosed technology as viewed from a rear surface side.

FIG. 1B is a view (X-Z plan view) of the CT apparatus 10 viewed from a rear surface side (a side opposite to the installation side of the examination table 16). A sterilization unit 20 that sterilizes the contact surface 17 is attached to a rear surface of the gantry 11. The sterilization unit 20 has an elongated rod-like shape, and one end thereof is attached to the gantry 11. A rotation shaft 18 with the Y direction as an axial direction is provided in the attachment portion of the sterilization unit 20, and the sterilization unit 20 is rotatable about an axis of the rotation shaft 18.

In a case where the contact surface 17 is sterilized, the sterilization unit 20 is brought into a first state of being brought into contact with or close to the contact surface 17 (a state in which a sterilization process can be performed). That is, as indicated by a solid line in FIGS. 1A and 1B, the sterilization unit 20 is positioned such that a longitudinal direction thereof is along the X direction to cross the opening portion 12 of the gantry 11. On the other hand, in a case where a radiation image is captured by the CT apparatus 10, that is, in a normal use of the CT apparatus 10, the sterilization unit 20 is brought into a second state (retracted state) of being separated from the contact surface 17. That is, as shown by the dotted lines in FIGS. 1A and 1B, the sterilization unit 20 is positioned such that the longitudinal direction thereof is along the Y direction so as not to hinder the movement of the bed portion 16B.

Figure 2:
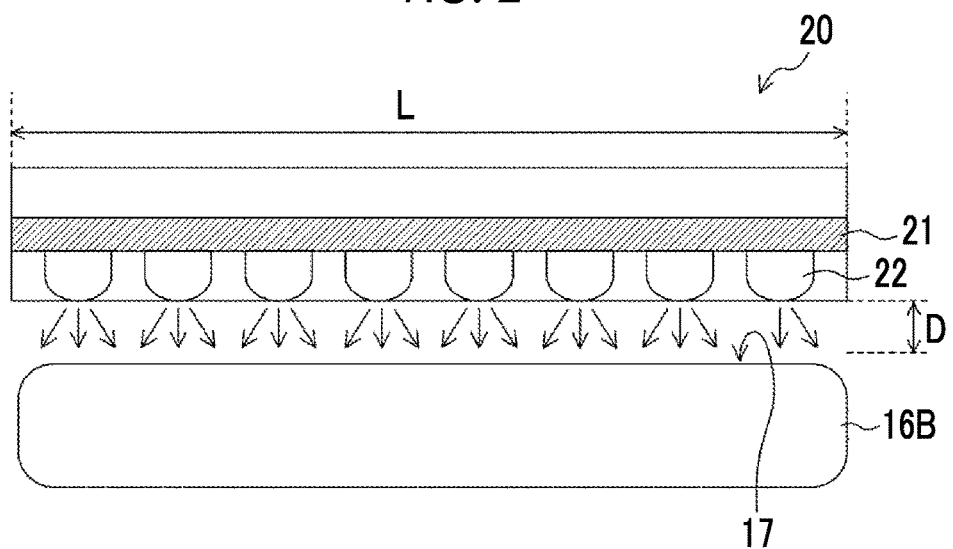
FIG. 2 is a diagram showing an example of a configuration of a sterilization unit according to the embodiment of the disclosed technology.

FIG. 2 is a diagram showing an example of a configuration of the sterilization unit 20. The sterilization unit 20 includes a plurality of light sources 22 that are arranged on a wiring board 21 and emit light having a bactericidal action. The contact surface 17 of the examination table 16 is irradiated with light from the light source 22 and thus the contact surface 17 can be sterilized. As the light source 22, for example, a light emitting diode (LED) that emits ultraviolet rays (UV-C) having a wavelength of 200 to 280 nm may be used. For example, by applying ultraviolet rays having a wavelength of 265 nm at 1.7 mJ/cm$^2$, it is possible to kill 99.9% of the human coronavirus. A mercury lamp may also be used as the light source 22 that emits ultraviolet rays.

A length L of the sterilization unit 20 in the longitudinal direction is preferably the equal to or less than a length of the contact surface 17 in the X direction. The sterilization unit 20 may include a lens that collects light from the light source 22. However, in a case where a UV-C wave is used as light having a bactericidal action, a material of the lens is limited to a material (for example, quartz and sapphire) that can transmit the UV-C wave therethrough, and thus the cost is high. In a case where a lens is not used, it is preferable that a distance between the sterilization unit 20 and the contact surface 17 is as short as possible. In order to perform effective sterilization, a distance D between the sterilization unit 20 and the contact surface 17 is preferably 10 cm or less, more preferably 5 cm or less, and most preferably 2 cm or less. In a case where the bed portion 16B can be lifted and lowered in the Z direction, the distance D between the sterilization unit 20 and the contact surface 17 may be adjusted by adjusting a height position of the bed portion 16B.

Figure 3:
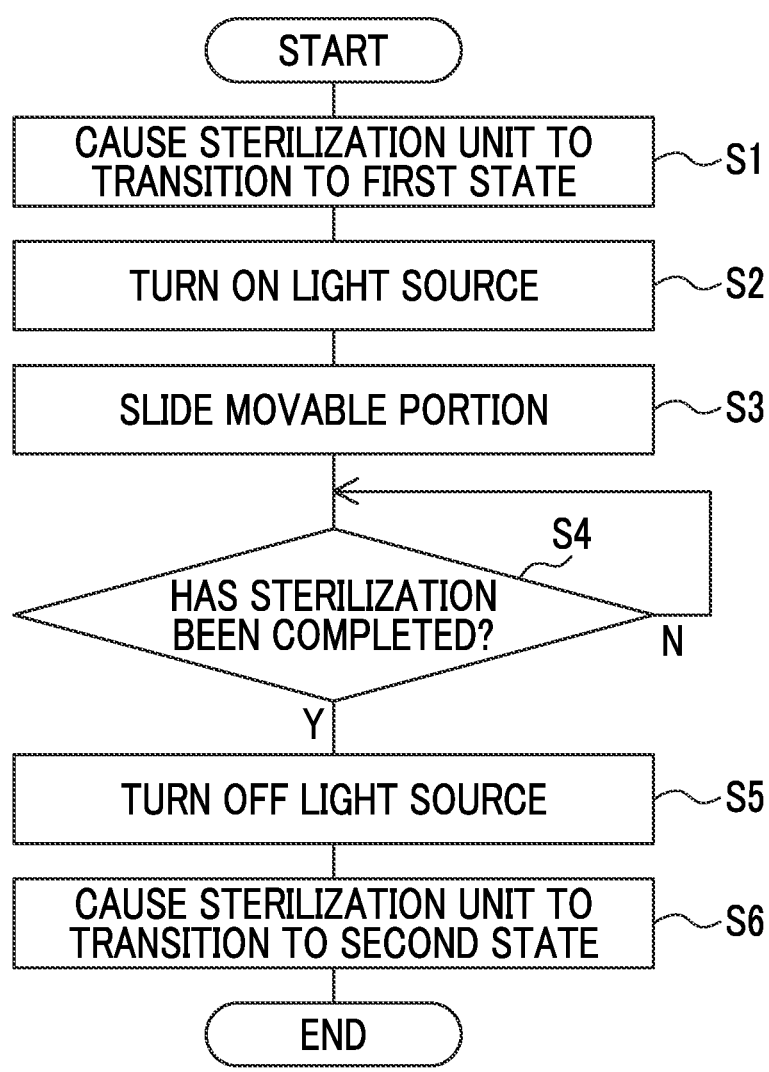
FIG. 3 is a flowchart showing an example of a flow of a sterilization process performed by a control unit according to the embodiment of the disclosed technology.

FIG. 3 is a flowchart showing an example of a flow of a sterilization process performed by the control unit 15 in a case where the contact surface 17 is sterilized. The sterilization process is executed, for example, in a case where a user performs an operation for starting the sterilization process. The operation for starting the sterilization process is performed by using, for example, an operation unit or a console (neither of that is shown) provided in the CT apparatus 10.

In step S1, the control unit 15 causes a state of the sterilization unit 20 to transition to the first state (a state in which the sterilization process can be performed). Consequently, the sterilization unit 20 is positioned such that the longitudinal direction thereof is along the X direction. In step S2, the control unit 15 turns on the light source 22 of the sterilization unit 20. In step S3, the control unit 15 slides the bed portion 16B of the examination table 16.

Figure 4:
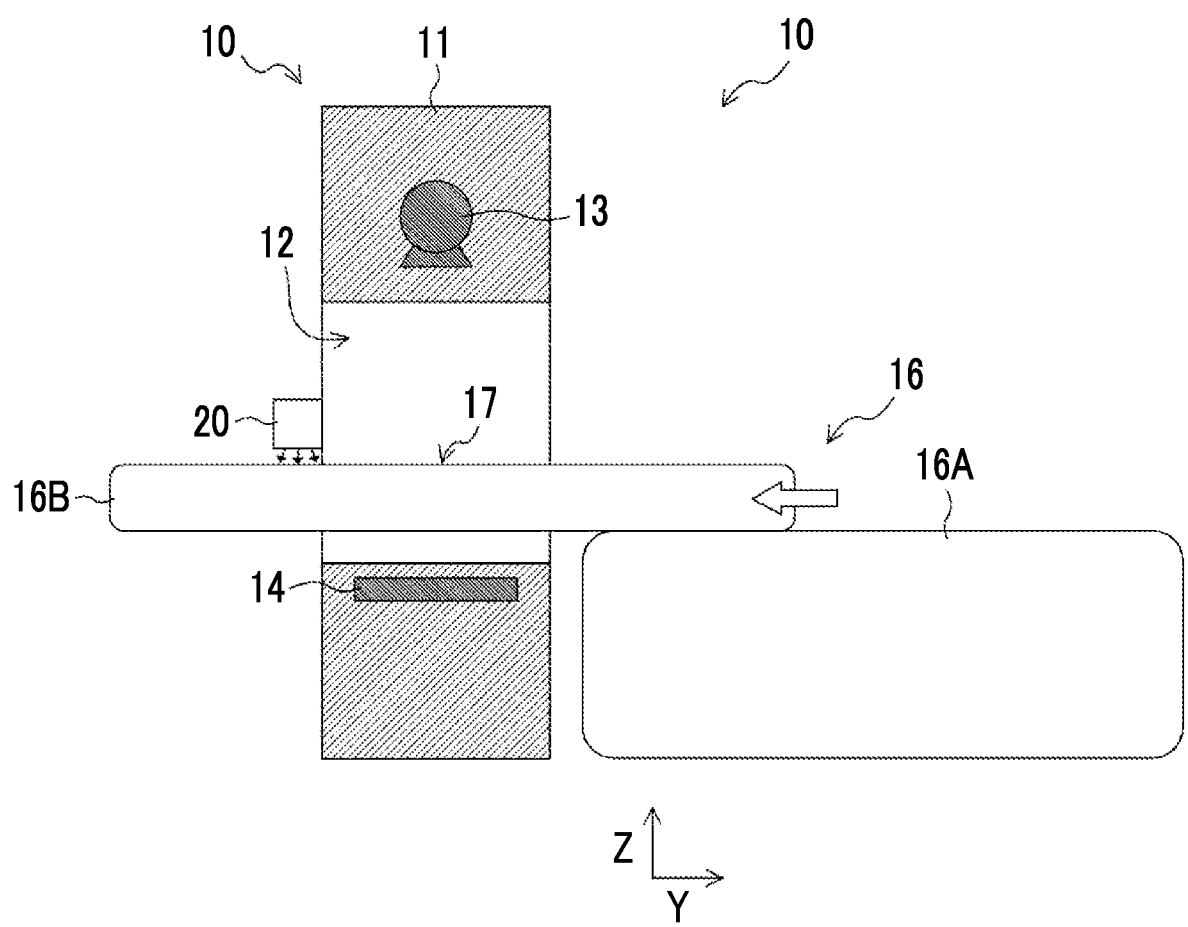
FIG. 4 is a diagram showing an operation of a bed portion during the sterilization process according to the embodiment of the disclosed technology.

FIG. 4 is a diagram (Y-Z sectional view) showing an operation of the bed portion 16B during the sterilization process. As shown in FIG. 4, the control unit 15 slides the bed portion 16B while maintaining the first state of the sterilization unit 20. Consequently, regions of the contact surface 17 that pass directly under the sterilization unit 20 are moved sequentially, and thus it is possible to irradiate the entire contact surface 17 with light having a bactericidal action emitted from the sterilization unit 20. In a case where the gantry 11 is movable along the Y direction, the gantry 11 may be moved together with the sterilization unit 20 in order to irradiate the entire contact surface 17 with the light from the sterilization unit 20.

In step S4, the control unit 15 determines whether or not sterilization of the contact surface 17 has been completed. In the control unit 15, for example, in a case where the bed portion 16B reaches a terminal position on the rear surface side of the gantry 11 and then returns to an initial position (that is, in a case where the bed portion 16B reciprocates once), it is determined that the sterilization has been completed. In a case where the control unit 15 determines that the sterilization of the contact surface 17 has been completed, the process proceeds to step S5.

In step S5, the control unit 15 turns off the light source 22. In step S6, the control unit 15 causes a state of the sterilization unit 20 to transition to the second state (retracted state). Consequently, the control unit 15 positions the sterilization unit 20 such that the longitudinal direction thereof is along the Y direction.

As described above, in the CT apparatus 10 according to the present embodiment, the first state in which the sterilization unit 20 is in contact with or close to the contact surface 17 and the second state in which the sterilization unit 20 is separated from the contact surface 17 can switch therebetween. In a case where the contact surface 17 is sterilized, by setting a state of the sterilization unit 20 to the first state, it is possible to effectively sterilize the contact surface 17. In a case where the contact surface 17 is not sterilized, by setting a state of the sterilization unit 20 to the second state, it is possible to avoid hindering the normal use of the CT apparatus 10 (that is, capturing a radiation image). That is, according to the CT apparatus 10 according to the present embodiment, it is possible to effectively sterilize the contact surface 17 without hindering the normal use of the CT apparatus 10.

Figure 5A:
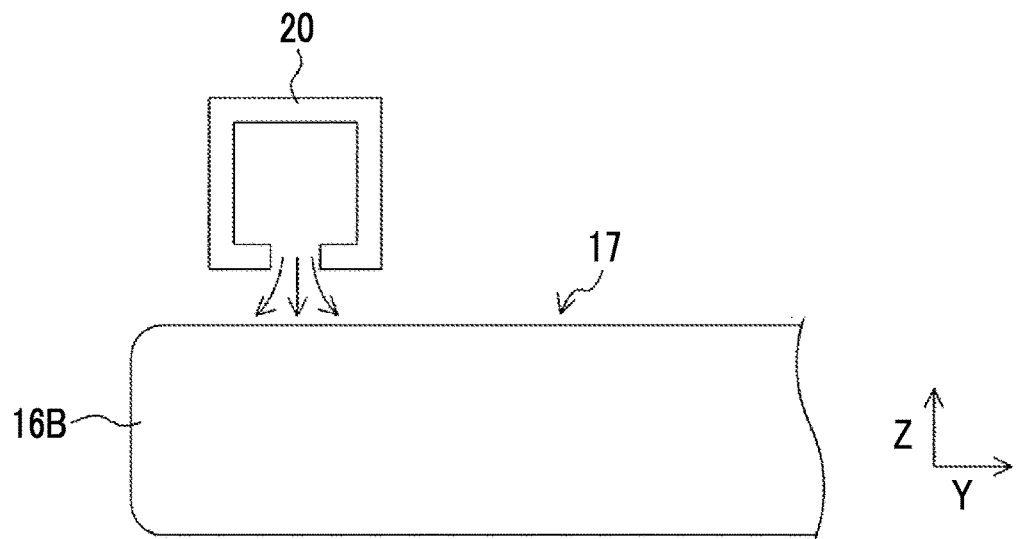
FIG. 5A is a diagram showing another example of the configuration of the sterilization unit according to the embodiment of the disclosed technology.
Figure 5B:
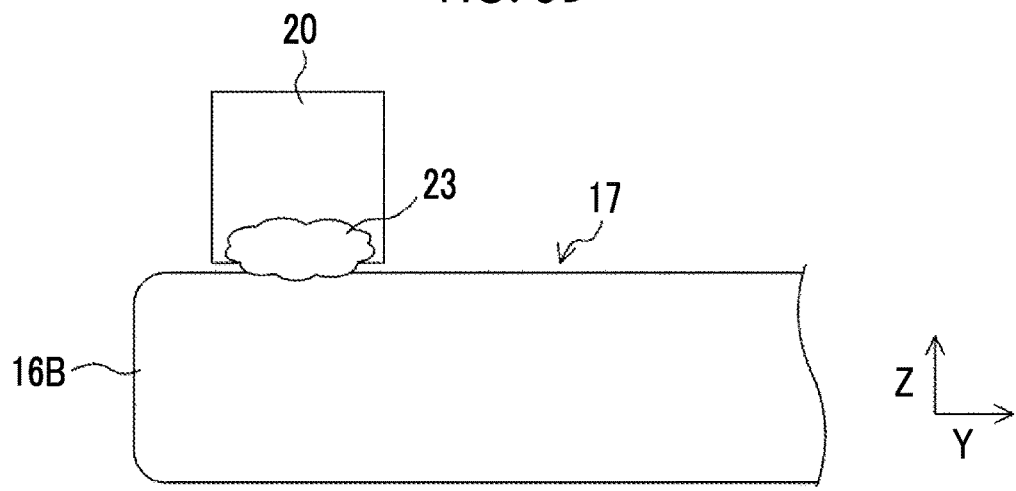
FIG. 5B is a diagram showing still another example of the configuration of the sterilization unit according to the embodiment of the disclosed technology.
Figure 5C:
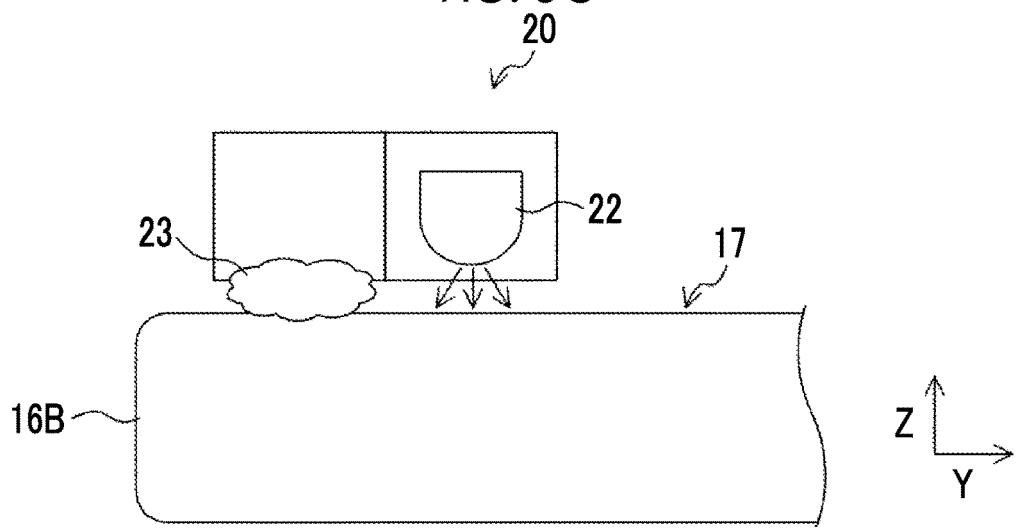
FIG. 5C is a diagram showing still another example of the configuration of the sterilization unit according to the embodiment of the disclosed technology.

In the above description, as an example, the sterilization unit 20 includes the light source 22 that emits light having a bactericidal action such as ultraviolet rays, but the present invention is not limited to this aspect. FIGS. 5A, 5B, and 5C are diagrams (Y-Z plan view) respectively showing other examples of a configuration of the sterilization unit 20.

As shown in FIG. 5A, the sterilization unit 20 may eject a gas or a liquid having a bactericidal action toward the contact surface 17. As the gas having a bactericidal action, for example, ozone or plasma may be used. As the liquid having a bactericidal action, for example, alcohol or a hypochlorous acid solution may be used. The sterilization unit 20 may be one that sprays aerosol that is a solid or liquid particle having a bactericidal action, dispersed in a gas.

As shown in FIG. 5B, the sterilization unit 20 may include a wiping member 23 that is a member impregnated with a liquid having a bactericidal action such as alcohol or a hypochlorous acid solution and wipes the contact surface 17. As the wiping member 23, a soft member such as a cloth or a sponge may be used.

As shown in FIG. 5C, the sterilization unit 20 may have a configuration in which a plurality of types of sterilization members different from each other are arranged along the Y direction that is the slide direction of the bed portion 16B. In the example shown in FIG. 5C, a configuration in which a light source 22 that emits light having a bactericidal action and a wiping member 23 impregnated with a liquid having a bactericidal action are arranged along the Y direction is exemplified. By arranging a plurality of types of sterilization members different from each other in the slide direction of the bed portion 16B, it is possible to promote the bactericidal action in the sterilization unit 20. A combination of a plurality of types of sterilization members may be selected as appropriate, and three or more types of sterilization members may be combined.

Figure 6:
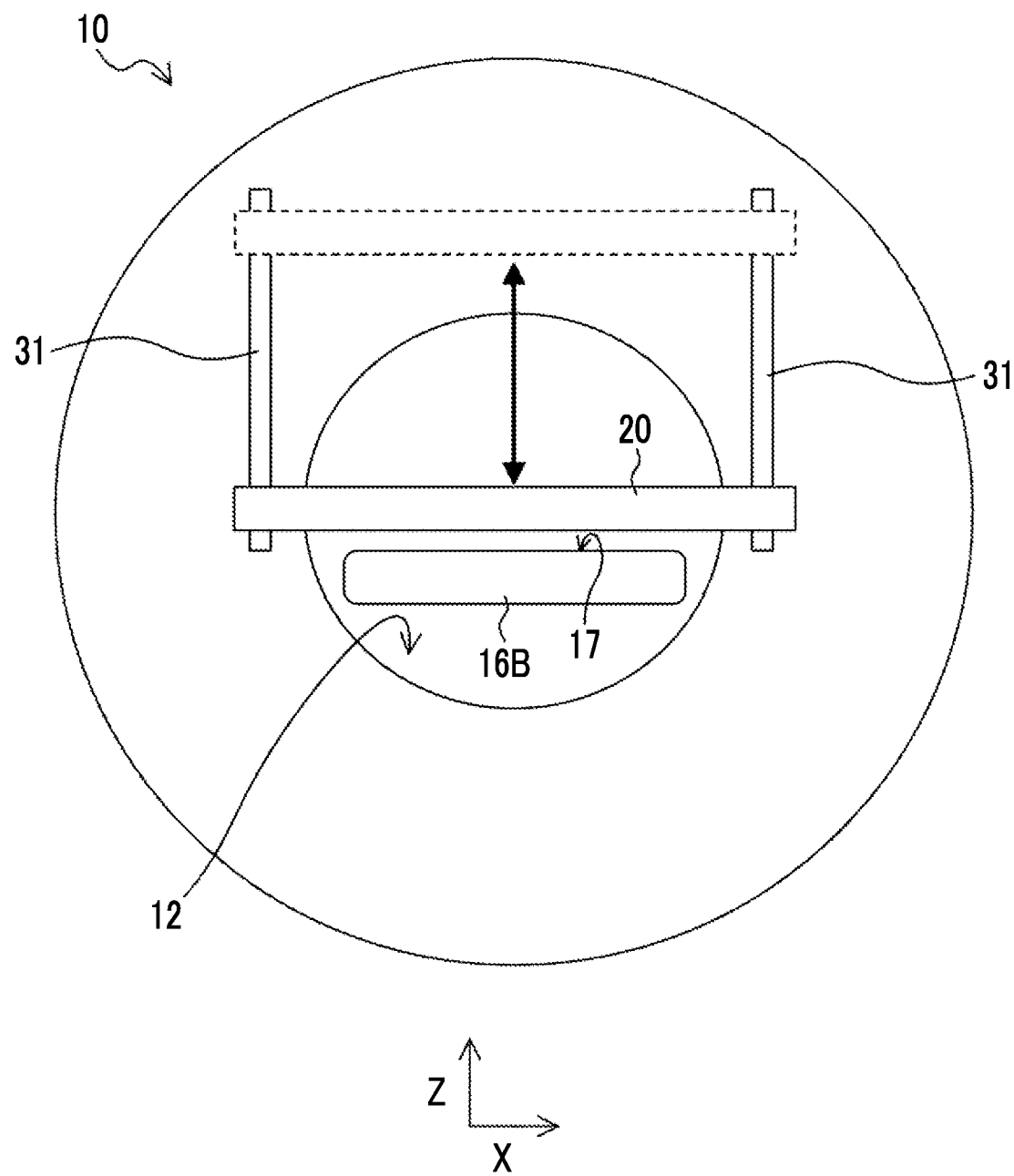
FIG. 6 is a view of a CT apparatus according to the embodiment of the disclosed technology as viewed from the rear surface side.

In the above description, a case where switching between the first state and the second state is performed by rotating the sterilization unit 20 about the axis of the rotation shaft 18 has been described as an example, but the present invention is limited to this aspect. For example, as shown in FIG. 6, switching between the first state and the second state may be performed by lifting and lowering the sterilization unit 20 in the Z direction along guide rods 31. In a case where the contact surface 17 is sterilized, the sterilization unit 20 is brought into the first state of being in contact with or close to the contact surface 17 (a state in which the sterilization process can be performed), and is positioned at a lowered position as indicated by a solid line in FIG. 6. On the other hand, in a case where a radiation image is captured by the CT apparatus 10, that is, in the normal use of the CT apparatus 10, the sterilization unit 20 is brought into the second state (retracted state) of being separated from the contact surface 17, and is positioned at a lifted position as indicated by a dashed line in FIG. 6.

Figure 7A:
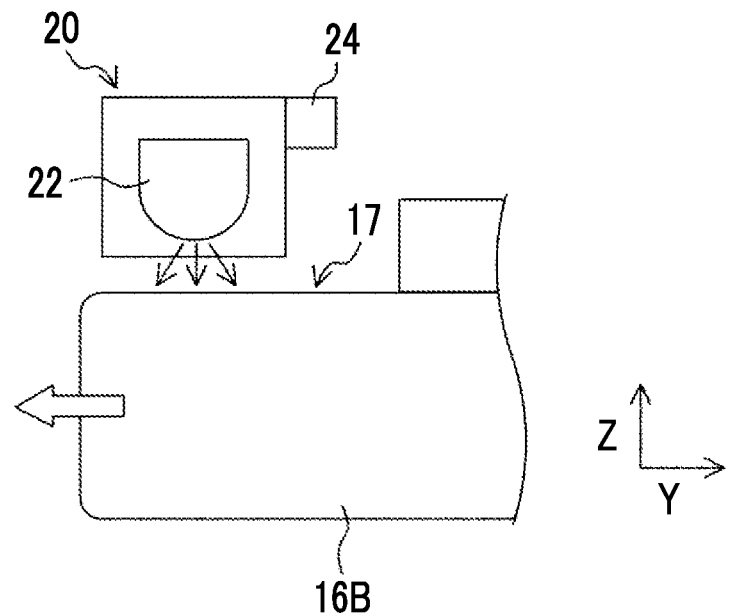
FIG. 7A is a diagram showing the sterilization unit including a height detection unit according to the embodiment of the disclosed technology.

As shown in FIG. 7A, the CT apparatus 10 may include a height detection unit 24 that detects a height of the contact surface 17. As the height detection unit 24, for example, a TOF camera that captures a distance image indicating a distance to an imaging target by using a time of flight (TOF) method may be used.

Figure 7B:
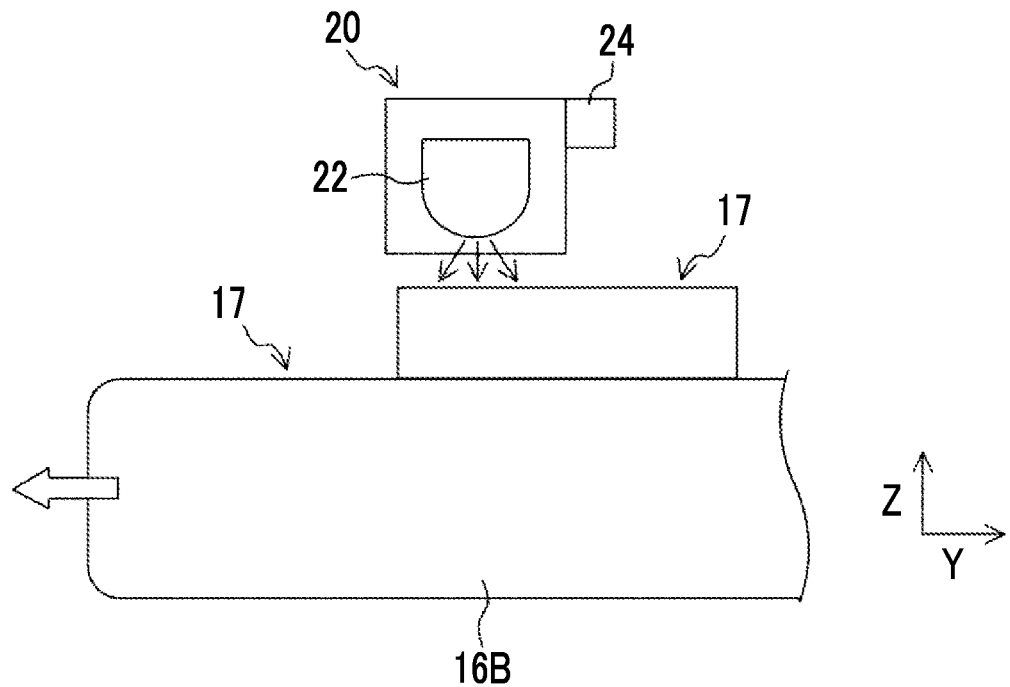
FIG. 7B is a diagram showing the sterilization unit including the height detection unit according to the embodiment of the disclosed technology.

In a case where the CT apparatus 10 includes the height detection unit 24, as shown in FIG. 7B, the control unit 15 may lift and lower the sterilization unit 20 in accordance with a change in a height of the contact surface 17 detected by the height detection unit 24 such that a distance between the sterilization unit 20 and the contact surface 17 is constant in the sterilization process. Consequently, even in a case where a structure such as a pillow is installed on the examination table 16 and the contact surface 17 has irregularities, a distance between the sterilization unit 20 and the contact surface 17 is kept constant, and thus the contact surface 17 can be appropriately sterilized. Although FIG. 7A and FIG. 7B exemplify a configuration in which the height detection unit 24 is attached to the sterilization unit 20, the height detection unit 24 may be attached to the opening portion 12 of the gantry 11.

In the above description, a case where the sterilization process is started on the basis of an operation of a user has been described as an example, but the sterilization process may be started on the basis of order information issued before a radiation image is captured by the CT apparatus 10. For example, in a case where the order information includes information related to a radiation image capturing schedule, the control unit 15 may start the sterilization process on the basis of the information related to the capturing schedule included in the order information. The control unit 15 may specify, for example, a timing after the end of imaging of a certain examinee and before the start of imaging of the next examinee, and start the sterilization process at that timing.

In the sterilization process, the control unit 15 may sterilize the contact surface 17 in a sterilization mode selected from a plurality of sterilization modes in which sterilization intensities are different from each other. For example, in a case where the sterilization unit 20 includes the light source 22 that emits ultraviolet rays, a sterilization intensity may be changed by changing at least one of an irradiation time, an irradiation range, or an irradiation intensity of the ultraviolet rays.

The irradiation time of the ultraviolet rays may be changed depending on, for example, a movement speed of the bed portion 16B that is being slid during the sterilization process. The irradiation time of the ultraviolet rays may also be changed depending on the number of times of reciprocation of the bed portion 16B during the sterilization process. The irradiation range of the ultraviolet rays may be changed depending on a movement range of the bed portion 16B that is being slid during the sterilization process. The irradiation intensity of the ultraviolet rays may be changed depending on, for example, a driving current of the light source 22 that emits the ultraviolet rays. The sterilization mode is selected through, for example, a user operation. A sterilization mode selection operation is performed by using, for example, an operation unit or a console (neither of that is shown) provided in the CT apparatus 10. As the sterilization mode, for example, three modes such as a standard mode, a high-speed mode, and an enhancement mode may be provided.

In a case where the standard mode is selected, in the sterilization process, the control unit 15 sets a movement speed of the bed portion 16B to a standard speed, and causes the bed portion 16B to reciprocate once to irradiate the entire contact surface 17 with ultraviolet rays.

In a case where the high-speed mode is selected, the control unit 15 sets a movement speed of the bed portion 16B to a speed higher than the standard speed in the sterilization process and restricts a movement range of the contact surface 17 to irradiate only a partial region of the contact surface 17 with ultraviolet rays. Consequently, a sterilization intensity is lower than in the standard mode, but the processing time is reduced. The high-speed mode is, for example, a mode that can be selected in a case where a large number of imaging orders are in a standby state.

In a case where the enhancement mode is selected, the control unit 15 sets a movement speed of the bed portion 16B to a speed slower than the standard speed in the sterilization process, and causes the bed portion 16B to reciprocate a plurality of times such that a process of irradiating the entire contact surface 17 with ultraviolet rays is repeated a plurality of times. Consequently, although the processing time is longer than that in the standard mode, a sterilization intensity is increased, and more reliable sterilization can be performed. The enhancement mode is, for example, a mode that can be selected in a case where the CT apparatus 10 is used for an examinee suspected of being infected with a pathogen.

Figure 8:
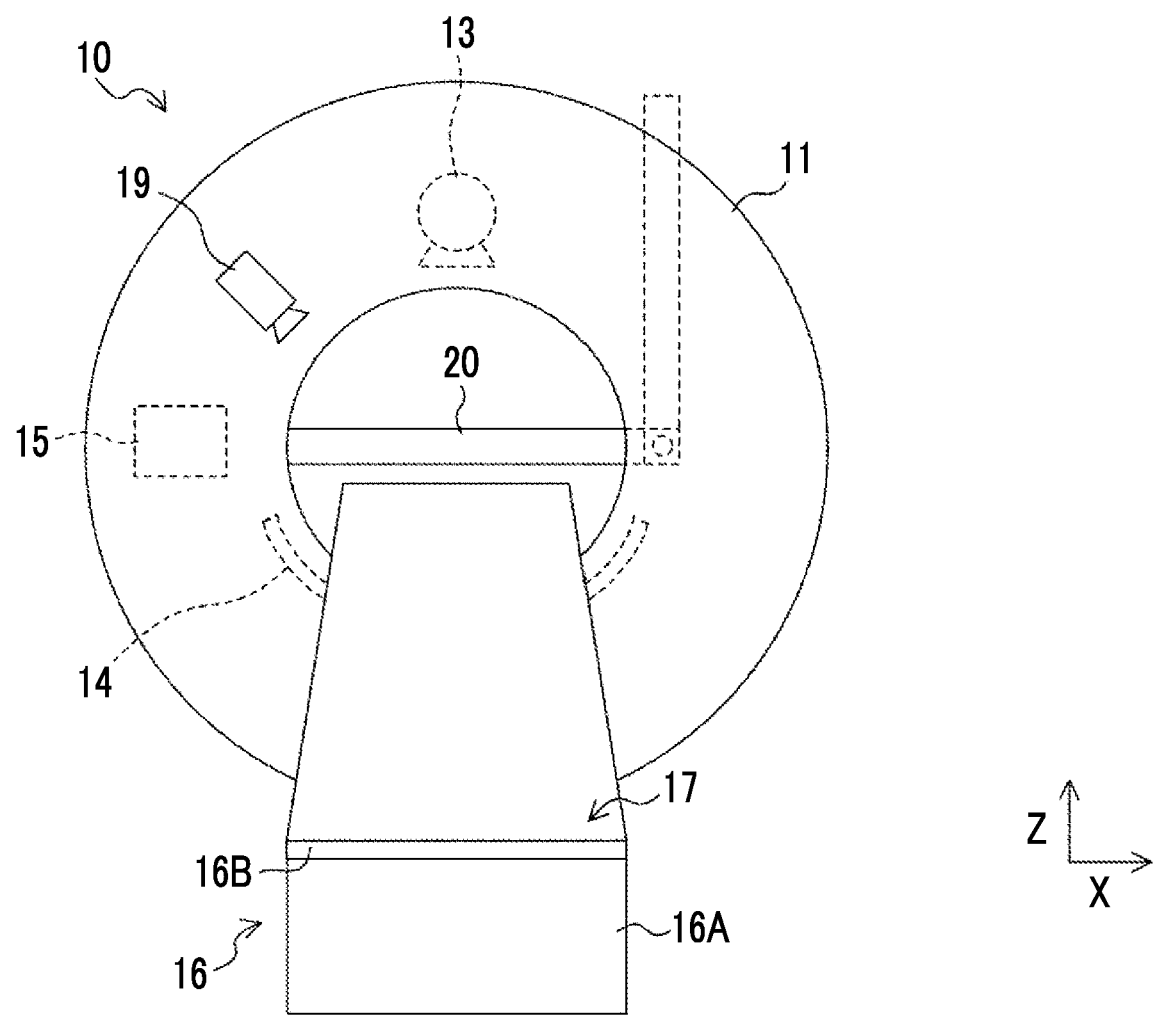
FIG. 8 is a diagram showing a CT apparatus including a region detection unit according to the embodiment of the disclosed technology.

As shown in FIG. 8, the CT apparatus 10 may include a region detection unit 19 that detects a contact region of contact surface 17 with which a subject (examinee) comes into contact. As the region detection unit 19, for example, a visible light camera installed such that the entire contact surface 17 is within an imaging visual field may be used. In a case where the CT apparatus 10 includes the region detection unit 19, the control unit 15 may set a sterilization intensity in a contact region detected by the region detection unit 19 in the sterilization process to be higher than that in a region other than the contact region, and sterilize the contact surface 17. For example, the control unit 15 may set a movement speed of the bed portion 16B in a case where the contact region passes directly under the sterilization unit 20 to be lower than a movement speed of the bed portion 16B in a case where a region other than the contact region passes directly under the sterilization unit 20. The control unit 15 may set an irradiation intensity of ultraviolet rays in a case where the contact region passes directly under the sterilization unit 20 to be higher than an irradiation intensity of ultraviolet rays in a case where a region other than the contact region passes directly under the sterilization unit 20. As described above, the contact surface 17 is sterilized by setting the sterilization intensity in the contact region to be higher than that in the region other than the contact region, and thus the sterilization process can be efficiently performed.

Figure 9A:
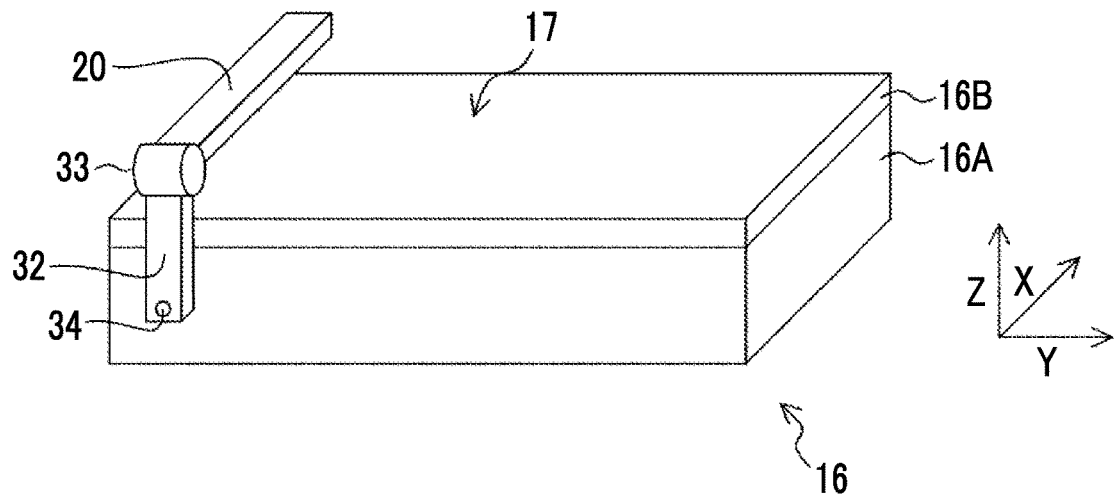
FIG. 9A is a diagram showing a configuration of the sterilization unit according to the embodiment of the disclosed technology.

In the above description, the configuration in which the sterilization unit 20 is attached to the gantry 11 has been described as an example. However, as shown in FIG. 9A, the sterilization unit 20 may be attached to the examination table 16. In the example shown in FIG. 9A, the sterilization unit 20 is attached to the base portion 16A of the examination table 16 via an arm portion 32. A rotation shaft 33 having the Y direction as an axial direction is provided between the sterilization unit 20 and the arm portion 32 in the state shown in FIG. 9A, and the sterilization unit 20 is rotatable about an axis of the rotation shaft 33. The arm portion 32 is rotatable about an axis of the rotation shaft 34 having the X direction as an axial direction.

Figure 9B:
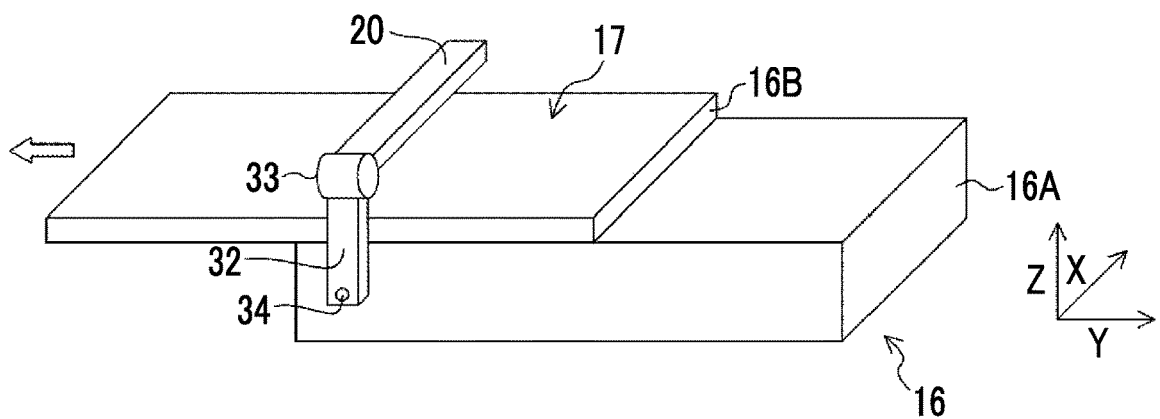
FIG. 9B is a diagram showing a configuration of the sterilization unit according to the embodiment of the disclosed technology.
Figure 9C:
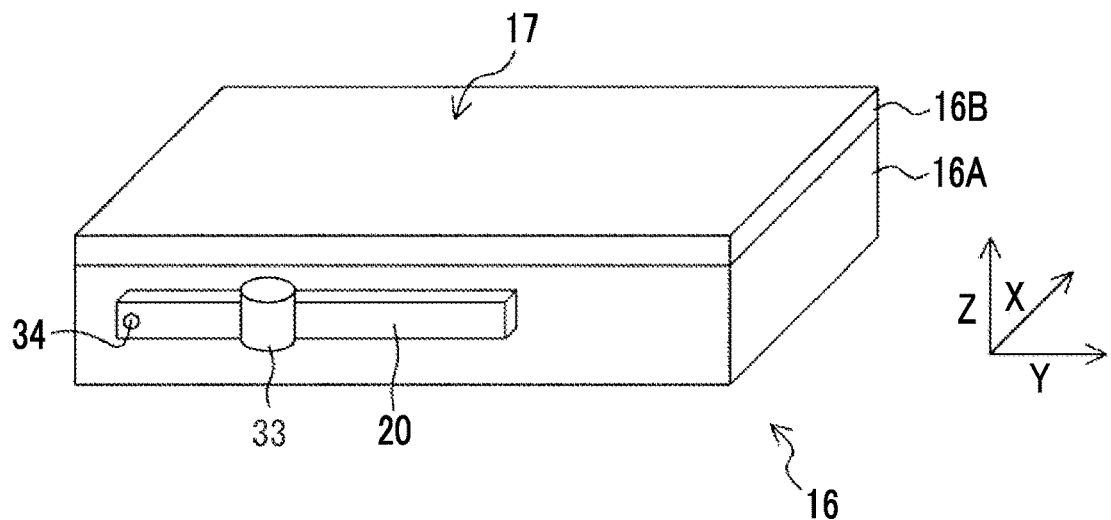
FIG. 9C is a diagram showing a configuration of the sterilization unit according to the embodiment of the disclosed technology.

In a case where the contact surface 17 is sterilized, the sterilization unit 20 is brought into a first state of being brought into contact with or close to the contact surface 17 (a state in which a sterilization process can be performed). That is, as shown in FIG. 9A, the arm portion 32 is positioned such that the longitudinal direction thereof is along the Z direction, and the sterilization unit 20 is positioned such that the longitudinal direction thereof is along the X direction. As shown in FIG. 9B, by sliding the bed portion 16B while setting a state of the sterilization unit 20 to the first state, it is possible to sterilize the entire contact surface 17. On the other hand, in a case where a radiation image is captured by the CT apparatus 10, that is, in a normal use of the CT apparatus 10, the sterilization unit 20 is brought into a second state (retracted state) of being separated from the contact surface 17. That is, as shown in FIG. 9C, the sterilization unit 20 is positioned such that the longitudinal direction thereof is along the longitudinal direction of the arm portion 32, and the arm portion 32 is positioned such that the longitudinal direction thereof is along the Y direction.

As described above, even in a configuration in which the sterilization unit 20 is attached to the examination table 16, the contact surface 17 can be effectively sterilized without hindering the normal use of the CT apparatus 10.

Figure 10A:
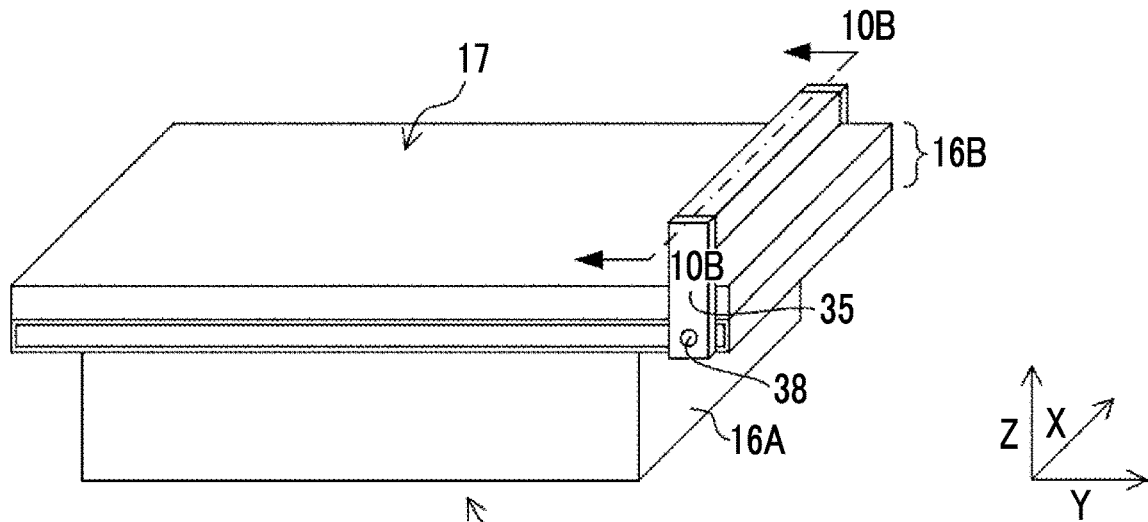
FIG. 10A is a diagram showing a configuration of the sterilization unit according to the embodiment of the disclosed technology.
Figure 10B:
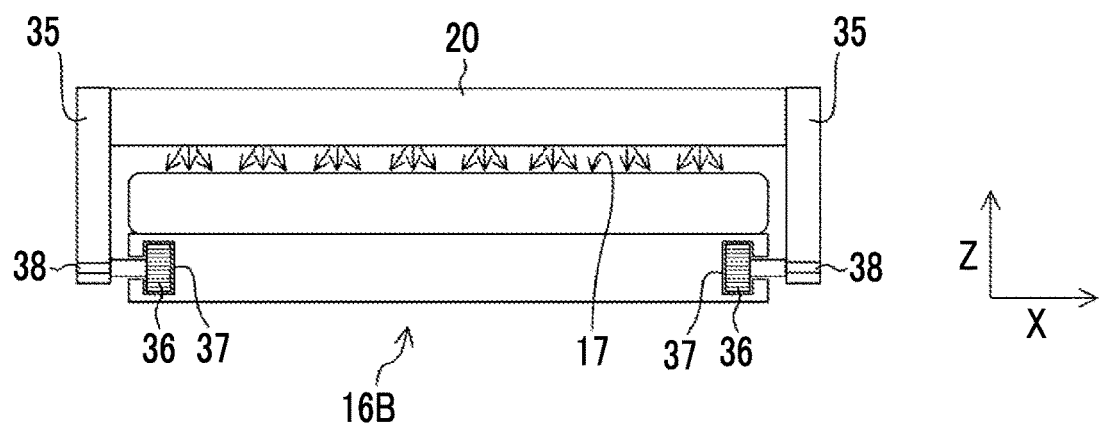
FIG. 10B is a diagram showing a configuration of the sterilization unit according to the embodiment of the disclosed technology.

FIG. 10A is a diagram showing another configuration example of the sterilization unit 20 attached to the examination table 16. FIG. 10B is a sectional view taken along the line 10B-10B in FIG. 10A. The sterilization unit 20 is attached to the examination table 16 via a pair of arm portions 35 attached to both ends in the longitudinal direction thereof. A roller 36 is provided at one end of the arm portion 35 in the longitudinal direction. The roller 36 is fitted in a guide groove 37 provided in the Y direction on the side surface of the bed portion 16B. By driving the roller 36 with a motor (not shown), the arm portions 35 can be moved together with the sterilization unit 20 in the Y direction. The arm portion 35 is rotatable about an axis of a rotation shaft 38 provided at the same position as the attachment position of the roller 36 with the X direction as an axial direction.

Figure 10C:
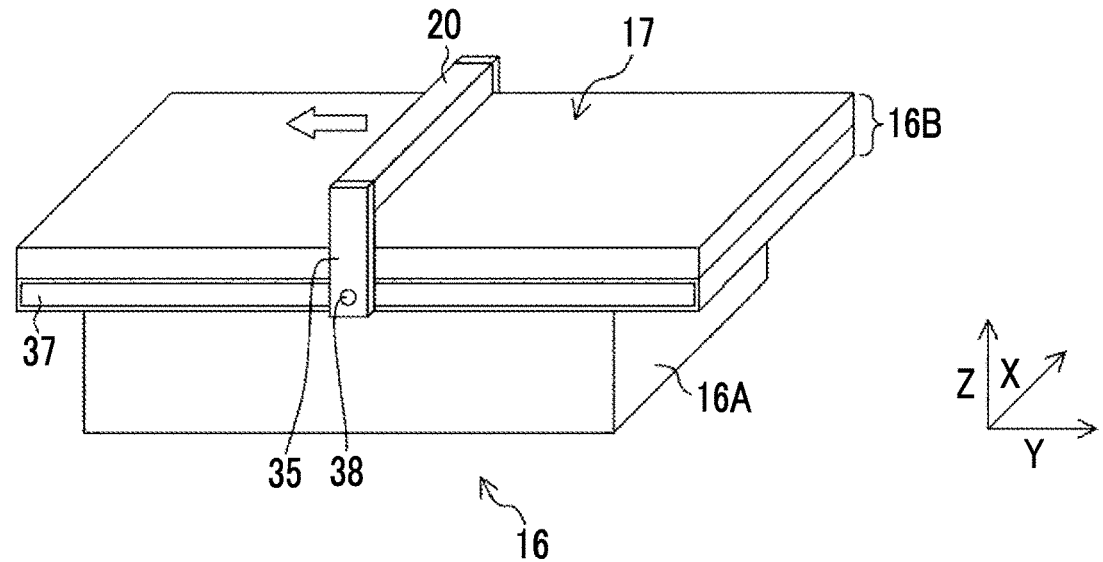
FIG. 10C is a diagram showing a configuration of the sterilization unit according to the embodiment of the disclosed technology.
Figure 10D:
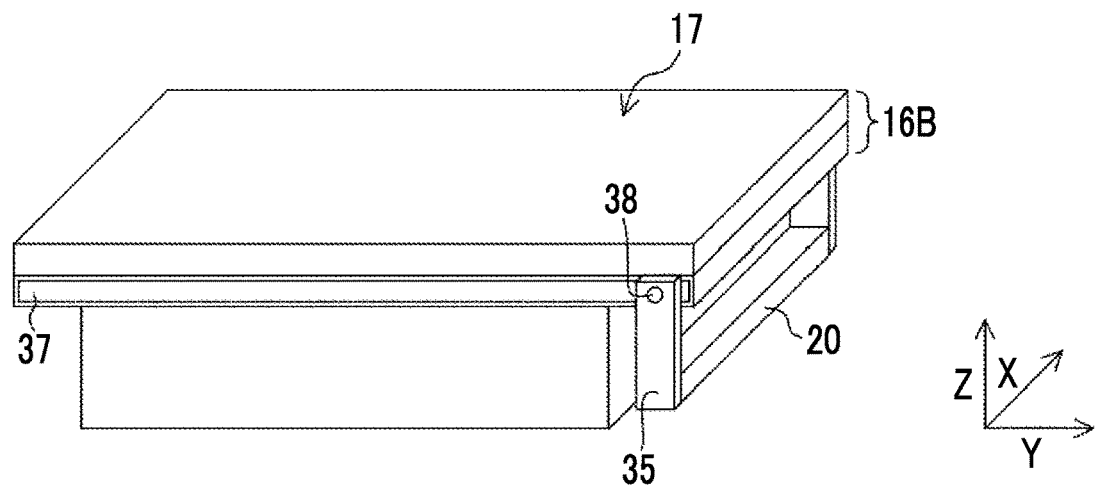
FIG. 10D is a diagram showing a configuration of the sterilization unit according to the embodiment of the disclosed technology.

In a case where the contact surface 17 is sterilized, the sterilization unit 20 is brought into a first state of being brought into contact with or close to the contact surface 17 (a state in which a sterilization process can be performed). That is, as shown in FIGS. 10A and 10B, the arm portion 35 is positioned such that the sterilization unit 20 is located above the bed portion 16B. As shown in FIG. 10C, by driving the roller 36 while setting a state of the sterilization unit 20 to the first state, the arm portion 35 is moved together with the sterilization unit 20 in the extension direction (Y direction) of the guide groove 37. Consequently, it is possible to sterilize the entire contact surface 17. On the other hand, in a case where a radiation image is captured by the CT apparatus 10, that is, in a normal use of the CT apparatus 10, the sterilization unit 20 is brought into a second state (retracted state) of being separated from the contact surface 17. That is, as shown in FIG. 10D, the arm portion 35 is positioned such that the sterilization unit 20 is located below the bed portion 16B.

As described above, even in a configuration in which the sterilization unit 20 is self-propelled, the contact surface 17 effectively sterilized without hindering the normal use of the CT apparatus 10. Even in a case where the CT apparatus 10 does not include a mechanism for sliding the bed portion 16B, it is possible to sterilize the entire contact surface 17 by applying this configuration.

Figure 11:
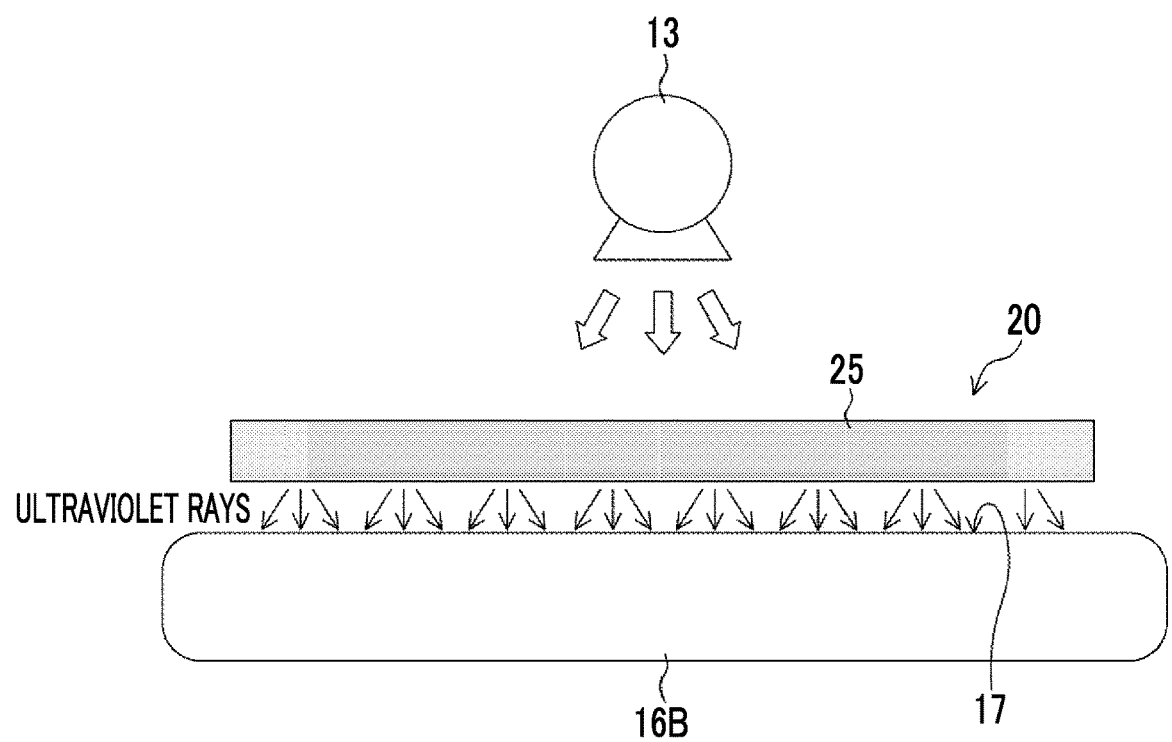
FIG. 11 is a diagram showing a configuration of the sterilization unit according to the embodiment of the disclosed technology.

FIG. 11 is a diagram showing another configuration of the sterilization unit 20. The sterilization unit 20 may include a phosphor 25 that absorbs radiation (X-rays) and emits ultraviolet rays. As radiation applied to the phosphor 25, X-rays radiated from the radiation source unit 13 are used. As the phosphor 25, for example, $Cs_2ZnCl_4$, $HfP_2O_7$, $BaFCl:Eu$, $BaFBr:Eu$, $YTaO_4$, or $Ba_2O_2S:Tb$ may be used.

Figure 12A:
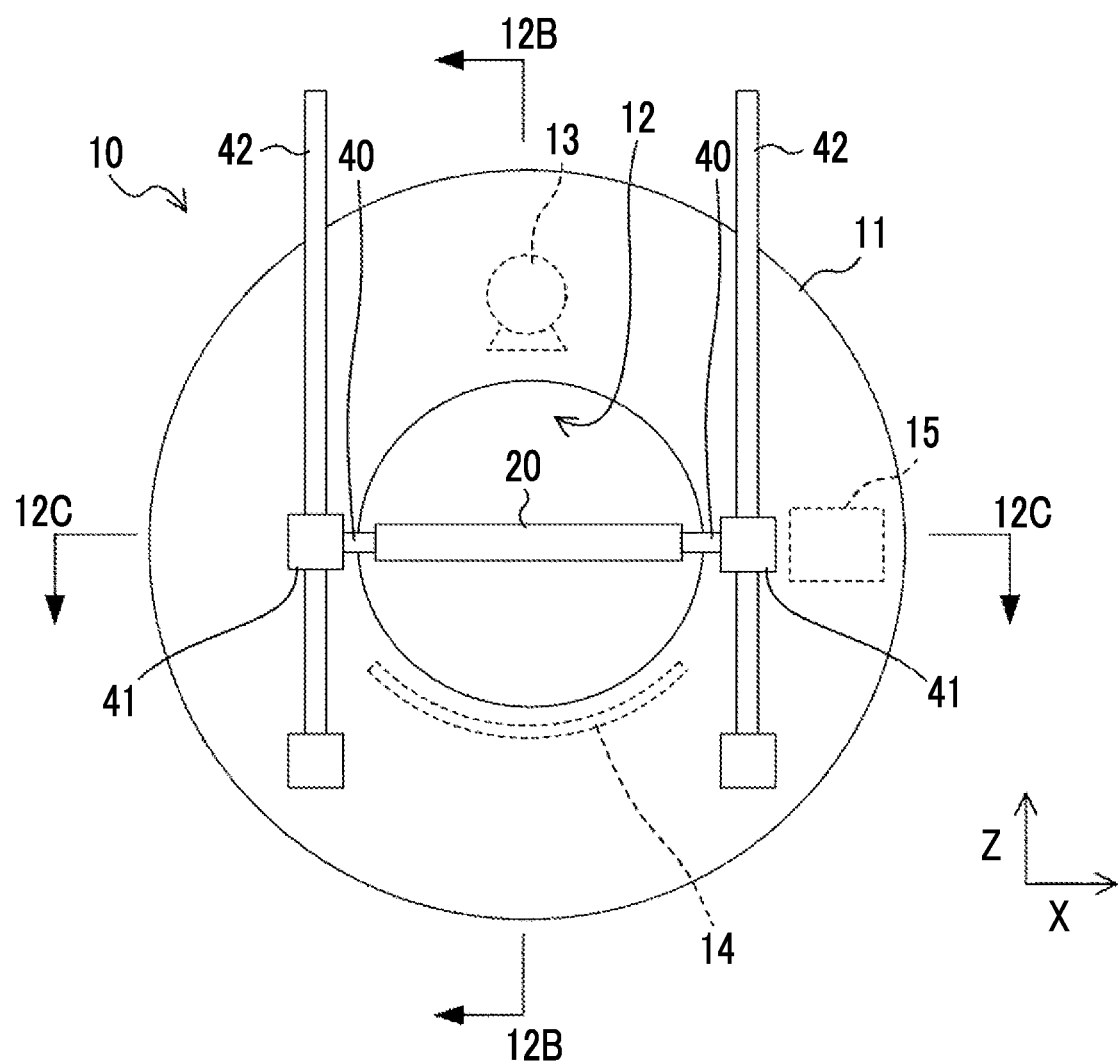
FIG. 12A is a diagram showing an example of a positioning mechanism of the sterilization unit including a phosphor according to the embodiment of the disclosed technology.
Figure 12B:
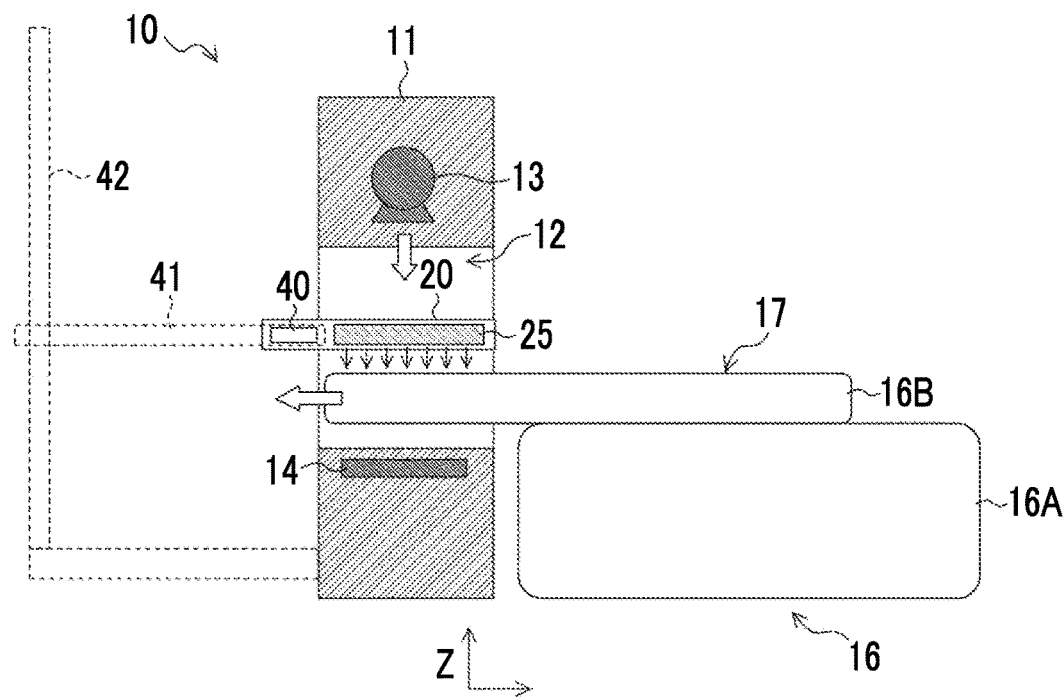
FIG. 12B is a diagram showing an example of the positioning mechanism of the sterilization unit including the phosphor according to the embodiment of the disclosed technology.

FIG. 12A is a diagram (X-Z plan view) showing an example of a positioning mechanism of the sterilization unit 20 including the phosphor 25. FIG. 12B is a sectional view (Y-Z sectional view) along the line 12B-12B in FIG. 12A, and FIG. 12C is a sectional view (X-Y sectional view) along the line 12C-12C in FIG. 12A.

Figure 12C:
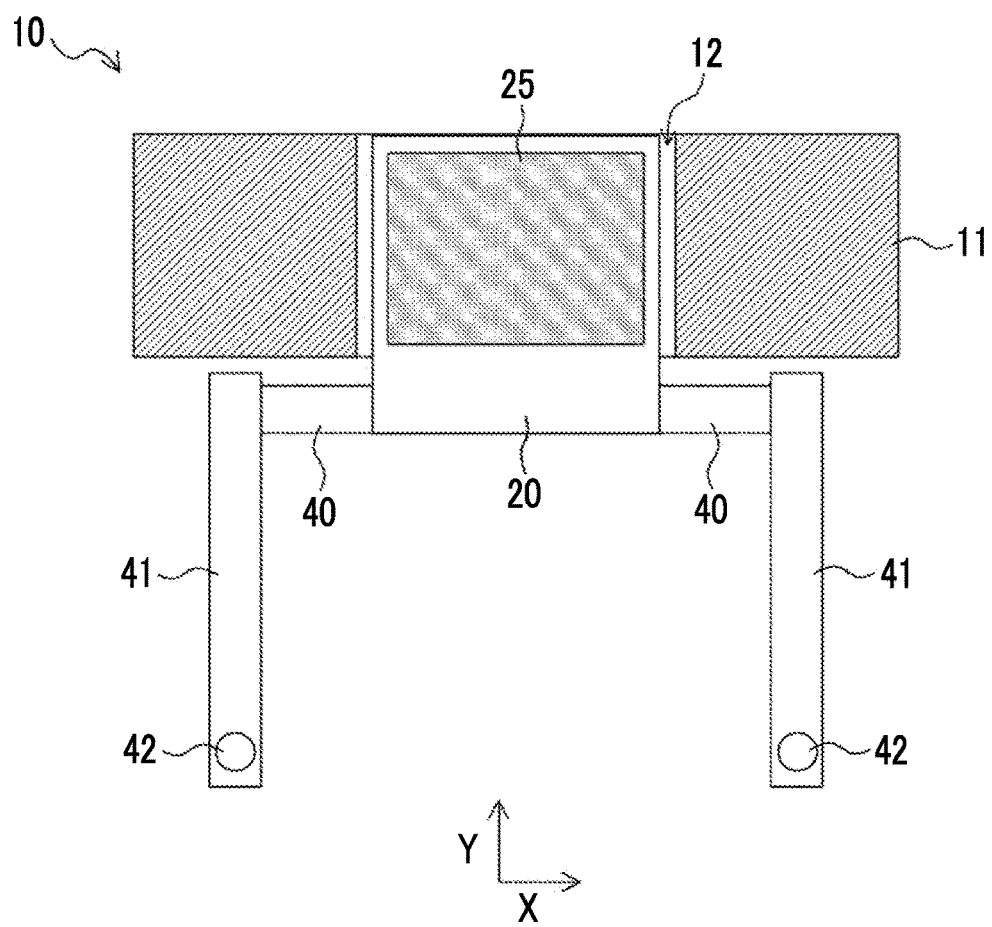
FIG. 12C is a diagram showing an example of the positioning mechanism of the sterilization unit including the phosphor according to the embodiment of the disclosed technology.

As shown in FIGS. 12A to 12C, the sterilization unit 20 including the phosphor 25 is attached to the gantry 11 via a support portion 40, a first guide rail 41, and a second guide rail 42. The second guide rail 42 includes a pair of rod-shaped members having the Z direction as a longitudinal direction, and is fixed to the rear surface of the gantry 11.

The first guide rail 41 includes a pair of rod-shaped members of which a longitudinal direction is the Y direction, and is slidably provided at the second guide rail 42. That is, the first guide rail 41 is movable (liftable and lowerable) in the Z direction. The support portion 40 is a member that supports the sterilization unit 20 at an end portion on the back side of the sterilization unit 20 (left side in FIG. 12B) and is slidably provided at the first guide rail 41. That is, the support portion 40 can be moved in the Y direction together with the sterilization unit 20.

In a case where the contact surface 17 is sterilized, the sterilization unit 20 is brought into a first state of being brought into contact with or close to the contact surface 17 (a state in which a sterilization process can be performed). That is, as shown in FIG. 12B, the first guide rail 41 is positioned at a height position near the center of the opening portion 12 of the gantry 11, and the support portion 40 is positioned at the terminal position on the front side of the first guide rail 41 (right side in FIG. 12B). Consequently, the sterilization unit 20 is disposed in the opening portion 12 of the gantry 11. On the other hand, the radiation source unit 13 is positioned such that the phosphor 25 is included in an irradiation field of X-rays. That is, the radiation source unit 13 is disposed directly above the phosphor 25.

In this state, by radiating X-rays from the radiation source unit 13, the X-rays are applied to the phosphor 25, and ultraviolet rays are emitted from the phosphor 25. The ultraviolet rays emitted from the phosphor 25 are applied to the contact surface 17 of the bed portion 16B. As shown in FIG. 12B, by sliding the bed portion 16B while setting a state of the sterilization unit 20 to the first state, it is possible to sterilize the entire contact surface 17. During the sterilization process, X-rays are continuously radiated from the radiation source unit 13.

Figure 12D:
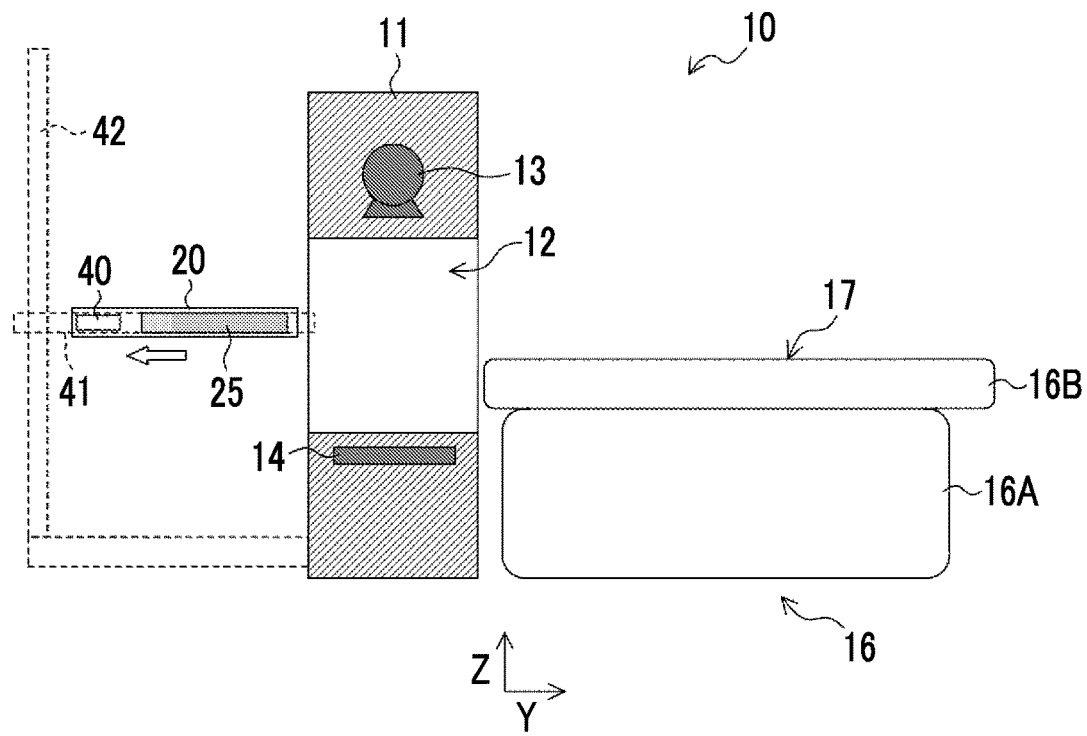
FIG. 12D is a diagram showing an example of the positioning mechanism of the sterilization unit including the phosphor according to the embodiment of the disclosed technology.
Figure 12E:
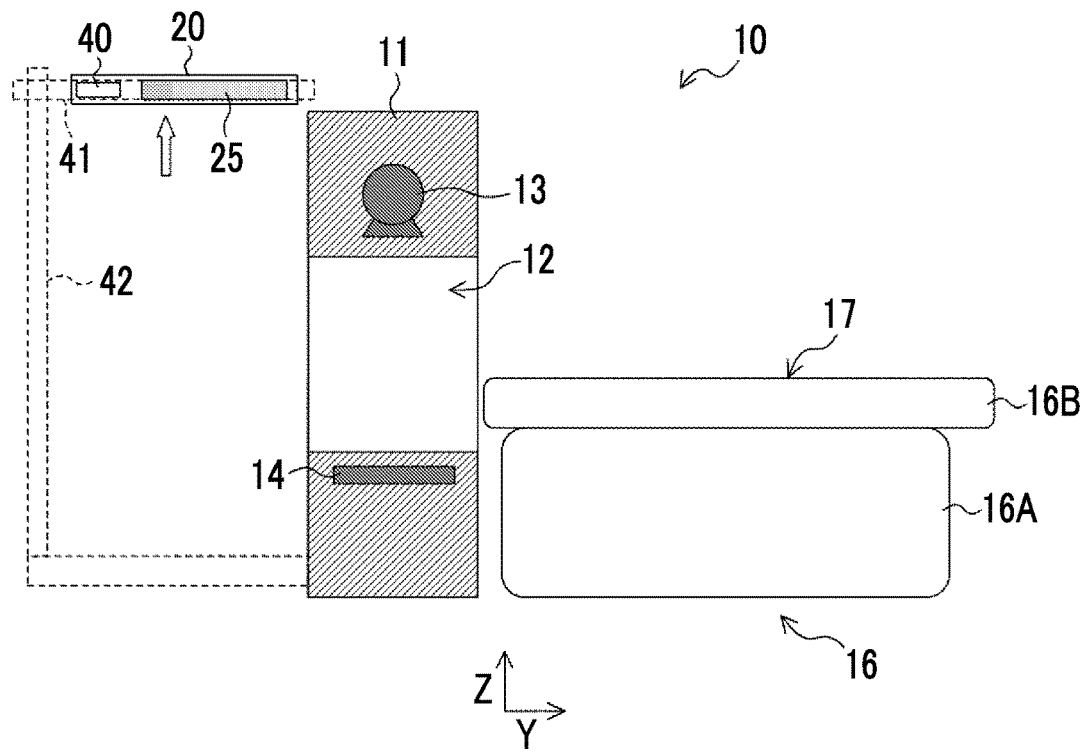
FIG. 12E is a diagram showing an example of the positioning mechanism of the sterilization unit including the phosphor according to the embodiment of the disclosed technology.
Figure 12F:
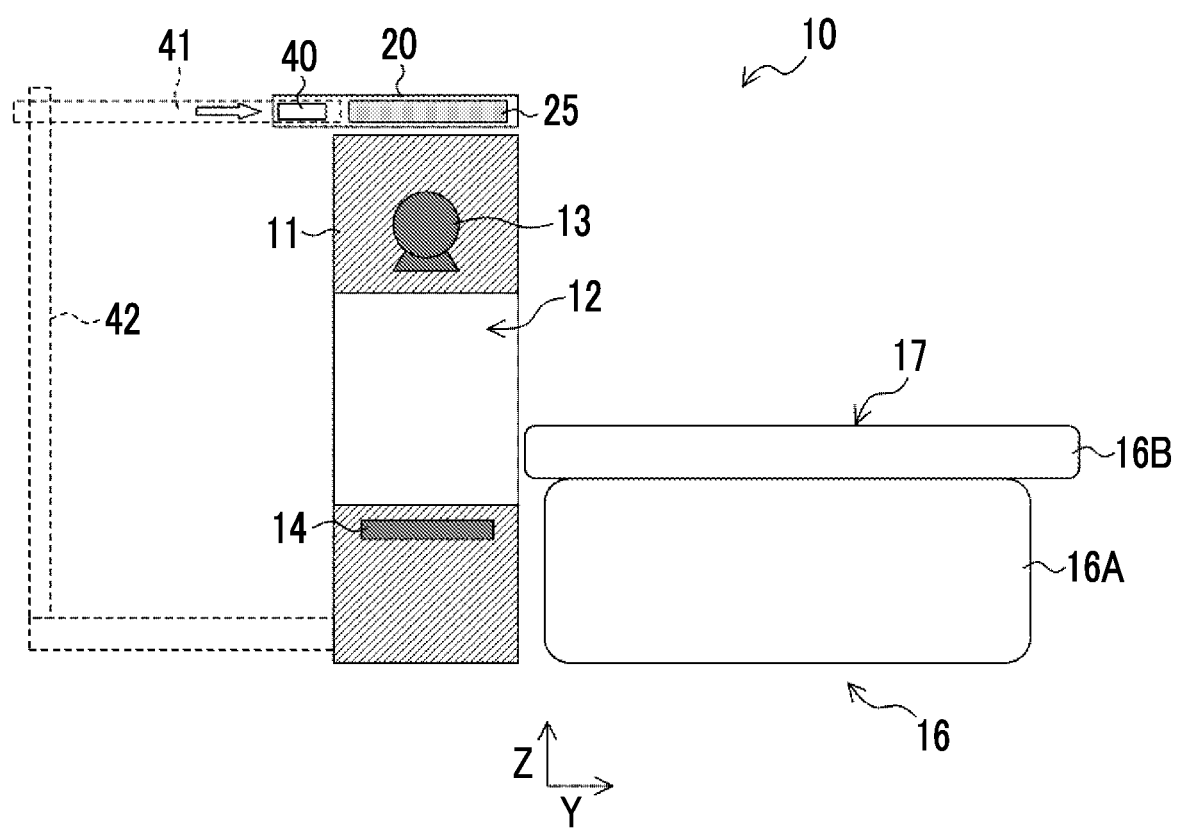
FIG. 12F is a diagram showing an example of the positioning mechanism of the sterilization unit including the phosphor according to the embodiment of the disclosed technology.

On the other hand, in a case where a radiation image is captured by the CT apparatus 10, that is, in a normal use of the CT apparatus 10, the sterilization unit 20 is brought into a second state (retracted state) of being separated from the contact surface 17. That is, in a case where the sterilization process has been completed, as shown in FIG. 12D, the support portion 40 is moved to the terminal position on the back side of the first guide rail 41 (left side in FIG. 12D). Thereafter, as shown in FIG. 12E, the first guide rail 41 is moved to the upper end position of the second guide rail 42, and then, as shown in FIG. 12F, the support portion 40 is moved to the terminal position on the front side of the first guide rail 42 (right side in FIG. 12F). Consequently, the sterilization unit 20 is disposed above the gantry 11.

Figure 13:
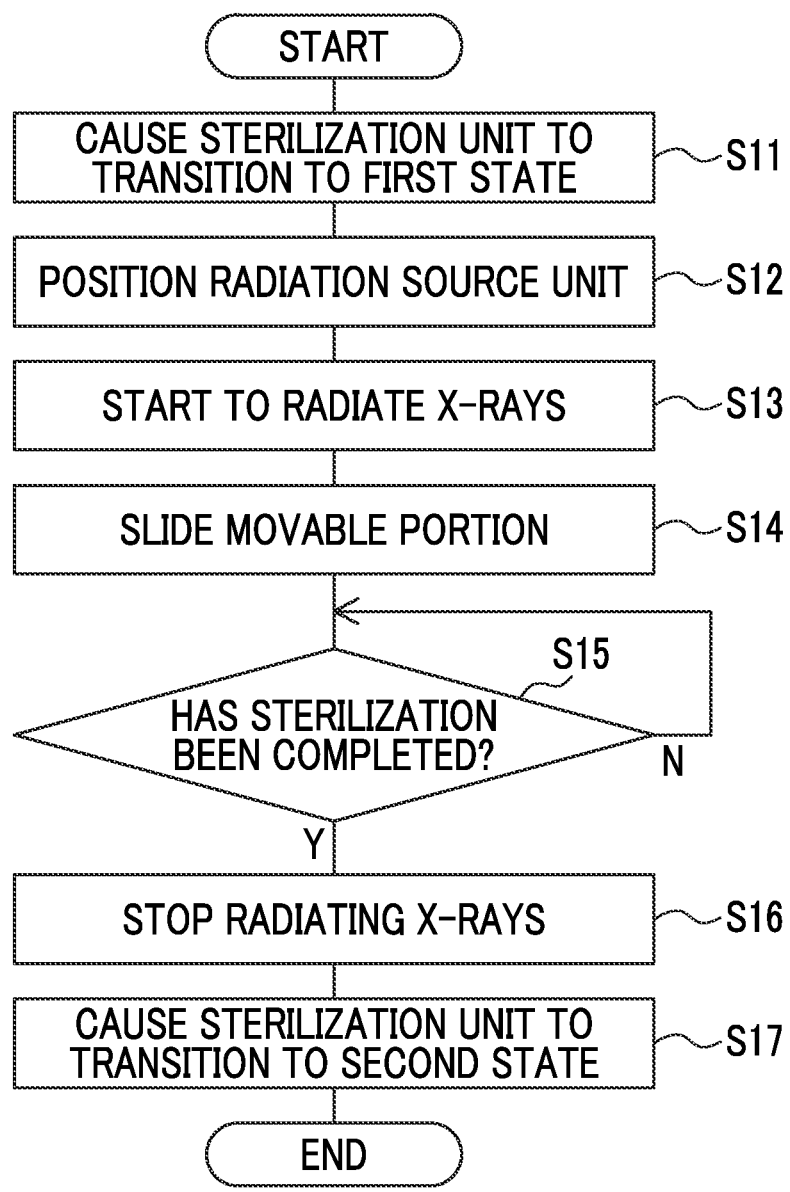
FIG. 13 is a flowchart showing an example of a flow of a sterilization process performed by the control unit according to the embodiment of the disclosed technology.

FIG. 13 is a flowchart showing an example of a flow of the sterilization process performed by the control unit 15 in a case where the contact surface 17 is sterilized in the CT apparatus 10 having the positioning mechanism of the sterilization unit 20 including the phosphor 25 described above.

In step S11, the control unit 15 causes a state of the sterilization unit 20 to transition to the first state shown in FIG. 12B. Consequently, the sterilization unit 20 including the phosphor 25 is disposed in the opening portion 12 of the gantry 11.

In step S12, the control unit 15 positions the radiation source unit 13 such that the phosphor 25 is included in the irradiation field of X-rays radiated from the radiation source unit 13. That is, the radiation source unit 13 is disposed directly above the phosphor 25.

In step S13, the control unit 15 causes the radiation source unit 13 to start to radiate X-rays. Consequently, the X-rays from the radiation source unit 30 are applied to the phosphor 25, and the phosphor 25 emits ultraviolet rays. The ultraviolet rays emitted from the phosphor 25 are applied to the contact surface 17. In step S14, the control unit 15 slides the bed portion 16B of the examination table 16. Consequently, the entire contact surface 17 is irradiated with the ultraviolet rays. During the period in which the bed portion 16B is being slid, X-rays are continuously emitted from the radiation source unit 13.

In step S15, the control unit 15 determines whether or not the sterilization of the contact surface 17 has been completed. In the control unit 15, for example, in a case where the bed portion 16B reaches a terminal position on the rear surface side of the gantry 11 and then returns to an initial position (that is, in a case where the bed portion 16B reciprocates once), it is determined that the sterilization has been completed. In a case where the control unit 15 determines that the sterilization of the contact surface 17 has been completed, the process proceeds to step S16.

In step S16, the control unit 15 stops radiating the X-rays from the radiation source unit 13. In step S16, a state of the sterilization unit 20 transitions to the second state (retracted state). Consequently, as shown in FIG. 12F, the sterilization unit 20 is disposed above the gantry 11.

As described above, even in a configuration in which the sterilization unit 20 includes the phosphor 25, the contact surface 17 can be effectively sterilized without hindering the normal use of the CT apparatus 10. As a configuration other than the configuration in which the sterilization unit including the phosphor 25 is configured with the guide rails 41 and 42, the sterilization unit may be configured with the arm as shown in FIGS. 10A to 10D. For sterilization, in a case where the bed portion 16B performs sterilization while traveling in the direction of the gantry (−Y direction) at a speed V, the arm having the sterilization unit 20 is moved in advance to the end of the bed portion 16B near the gantry 11. Next, the bed portion 16B is moved in the direction of the gantry 11 at the speed V for sterilization, and from a time at which the arm reaches the optimum position where X-rays are applied, which is the center position of the gantry, the arm is stopped at that position by moving the arm in the direction opposite to the gantry 11 (+Y direction) at the same speed V as that of the bed portion 16B, that is, by controlling a movement speed of the bed portion 16B and a movement speed of the arm to be the same and the traveling directions to be opposite to each other. Thus, the sterilization unit is constantly irradiated with X-rays, and the phosphor 25 that has absorbed the X-rays emits ultraviolet rays such that sterilization can be performed.

Figure 14:
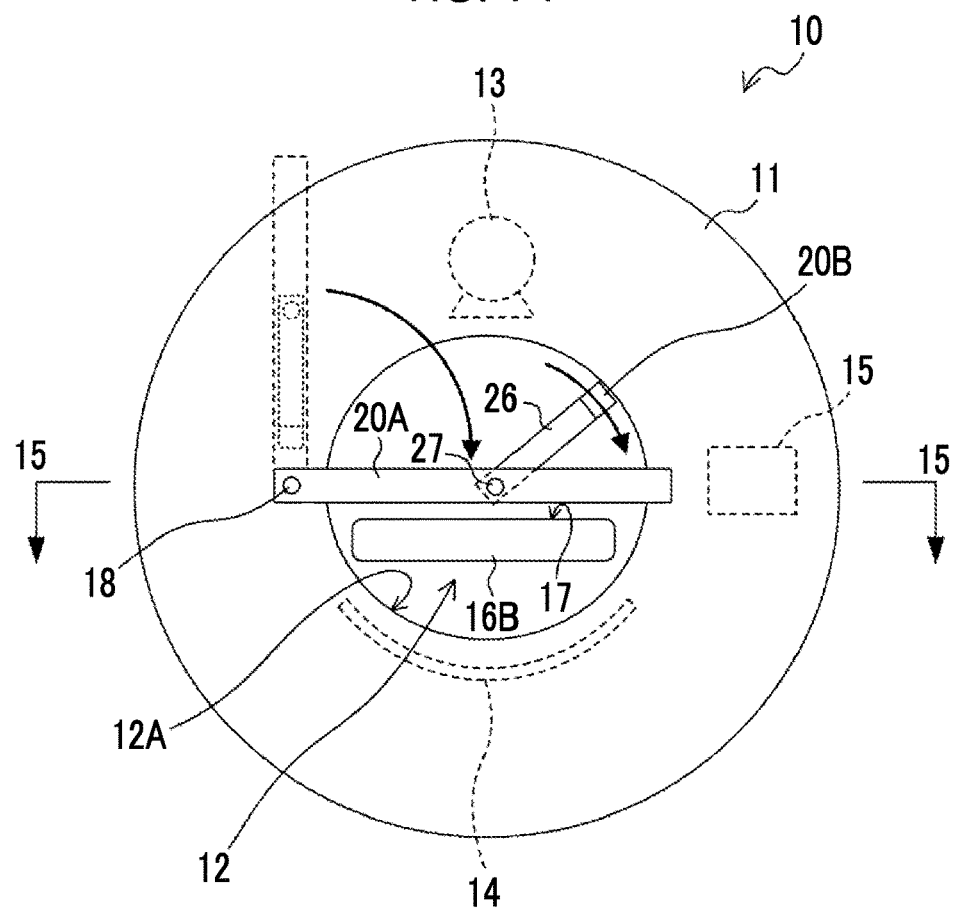
FIG. 14 is a diagram showing an example of a configuration of a CT apparatus including a second sterilization unit according to the embodiment of the disclosed technology.
Figure 15A:
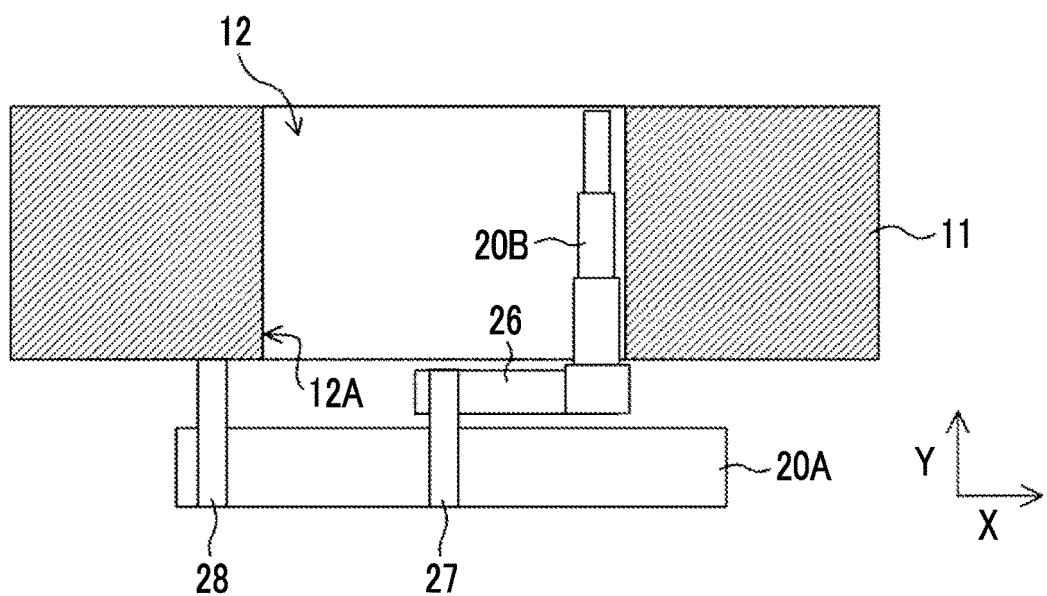
FIG. 15A is a sectional view taken along the line 15-15 in FIG. 14.
Figure 15B:
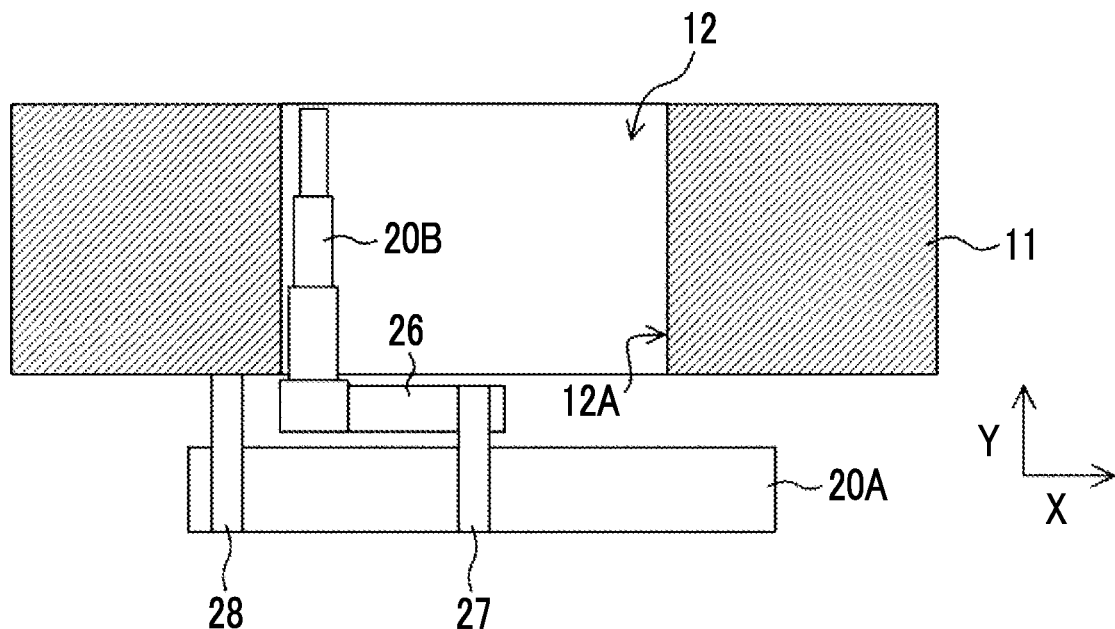
FIG. 15B is a sectional view taken along the line 15-15 in FIG. 14.
Figure 15C:
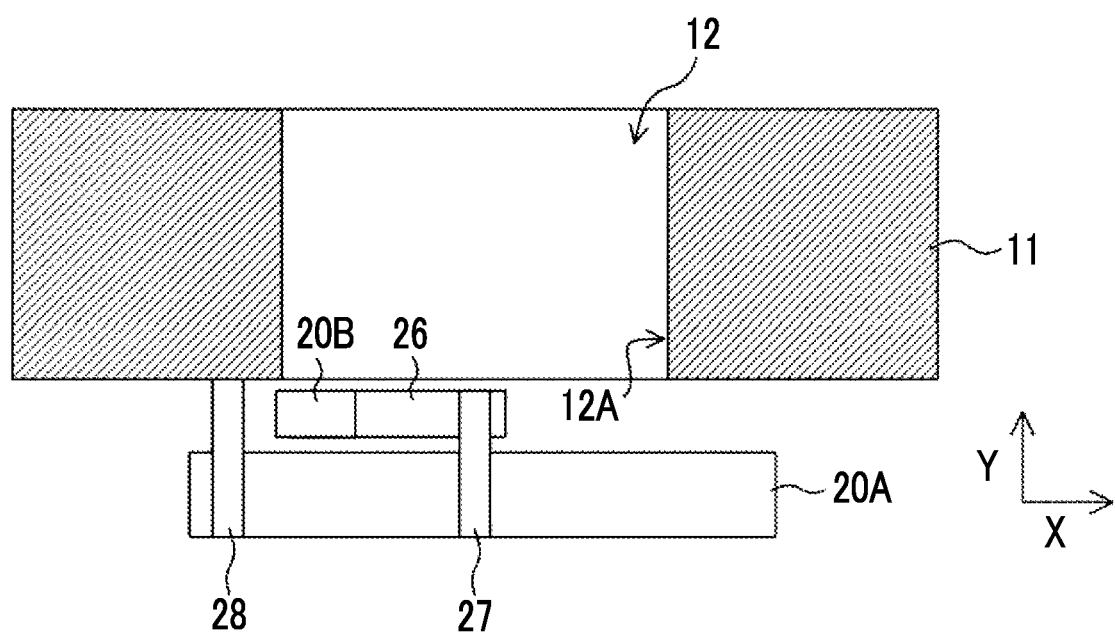
FIG. 15C is a sectional view taken along the line 15-15 in FIG. 14.

FIG. 14 is a diagram (X-Z plan view) showing an example of a configuration of the CT apparatus 10 including a second sterilization unit 20B that sterilizes an inner wall surface 12A of the opening portion 12 of the gantry 11. FIGS. 15A, 15B, and 15C each are sectional views (X-Y sectional views) taken along the line 15-15 in FIG. 14.

The second sterilization unit 20B is attached to a first sterilization unit 20A that sterilizes the contact surface 17 of the examination table 16. The first sterilization unit 20A corresponds to the sterilization unit 20 shown in FIGS. 1A and 1B. The second sterilization unit 20B is attached to the first sterilization unit 20A via an arm portion 26. The second sterilization unit 20B is attached to a distal end of the arm portion 26, and a basal end of the arm portion 26 is attached to the center of the first sterilization unit 20A in the longitudinal direction. A rotation shaft 27 having the Y direction as an axial direction is provided in the attachment part of the arm portion 26 to the first sterilization unit 20A, and the arm portion 26 is rotatable by 360° about an axis of the rotation shaft 27.

Figure 16A:
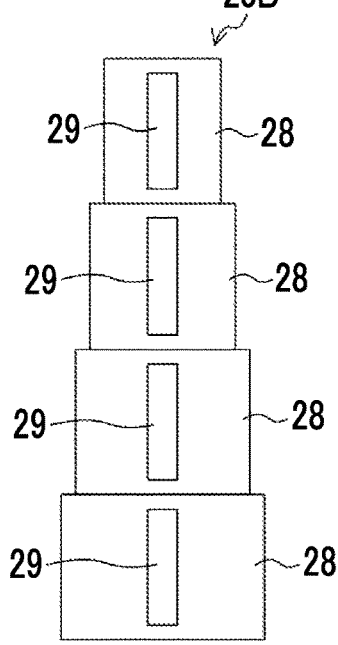
FIG. 16A is a diagram showing an example of a configuration of the second sterilization unit according to the embodiment of the disclosed technology.
Figure 16B:
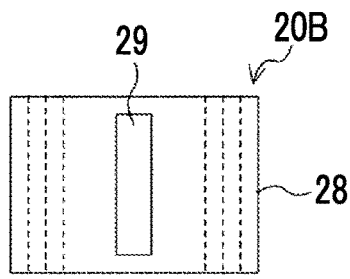
FIG. 16B is a diagram showing an example of a configuration of the second sterilization unit according to the embodiment of the disclosed technology.
Figure 16C:
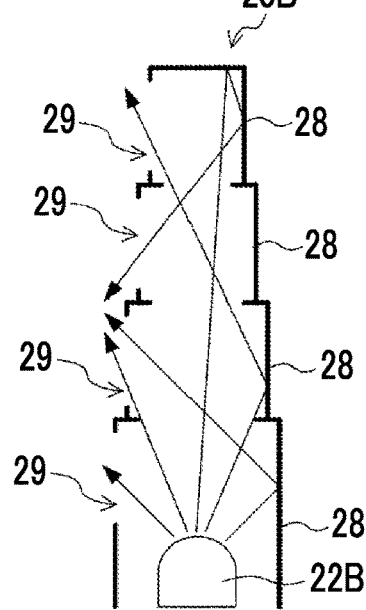
FIG. 16C is a diagram showing an internal structure of the second sterilization unit according to the embodiment of the disclosed technology.

FIGS. 16A and 16B are diagrams showing an example of a configuration of the second sterilization unit 20B, and FIG. 16C is a diagram showing an internal structure of the second sterilization unit 20B. The second sterilization unit 20B includes a plurality of tubular members 28 having diameters different from each other, and a light source 22B that is provided inside the tubular member 28 and emits light having a bactericidal action such as ultraviolet rays. The second sterilization unit 20B is extendable and contractible, and in the extended state shown in FIG. 16A, the plurality of tubular members 28 are disposed such that the diameters gradually decrease toward the distal end. On the other hand, in the contracted state shown in FIG. 16B, the tubular member 28 having a relatively small diameter is accommodated inside the tubular member 28 having a relatively large diameter.

An opening portion 29 is provided in each of the tubular members 28. An inner wall surface of the tubular member 28 is covered with a reflective film made of a member having light reflectivity such as aluminum. Consequently, as shown in FIG. 16C, the light emitted from the light source 22B is reflected by the inner wall surface of the tubular member 28 and emitted from the opening portion 29 to the outside of the tubular member 28. The opening portion 29 is disposed in a direction facing the inner wall surface 12A of the opening portion 12 of the gantry 11.

In a case where the inner wall surface 12A is sterilized by the second sterilization unit 20B, as shown in FIGS. 15A, 15B, and 16A, the second sterilization unit 20B is brought into an extended state, and the arm portion 26 is rotated about the axis of the rotation shaft 27. Consequently, as shown in FIGS. 15A and 15B, the second sterilization unit 20B is moved along the inner wall surface 12A while maintaining a state of being in contact with or close to the inner wall surface 12A. Consequently, the light emitted from the light source 22B is applied to the entire inner wall surface 12A.

On the other hand, in a case where a radiation image is captured by the CT apparatus 10, that is, in a normal use of the CT apparatus 10, as shown in FIGS. 15C and 16B, the second sterilization unit 20B is brought into a contracted state. Thereafter, as indicated by the dotted line in FIG. 14, the first sterilization unit 20A is positioned such that the longitudinal direction thereof is along the Z direction.

As described above, by providing the CT apparatus 10 with the second sterilization unit 20B in addition to the first sterilization unit 20A, not only the contact surface 17 of the examination table 16 but also the inner wall surface 12A of the opening portion 12 of the gantry 11 can also be sterilized. By making the arm portion 26 provided with the second sterilization unit 20B rotatable about the axis of the rotation shaft 27, it is possible to sterilize the entire inner wall surface 12A. By making the second sterilization unit 20B extendable and contractible, it is possible to perform the sterilization process without hindering the normal use of the CT apparatus 10.

In the above description, an aspect in which the second sterilization unit 20B includes the light source 22B that emits light having a bactericidal action has been described as an example, but the present invention is not limited to this aspect. For example, the second sterilization unit 20B may be one that ejects a gas having a bactericidal action such as ozone or plasma or a liquid having a bactericidal action such as alcohol or a hypochlorous acid solution. The second sterilization unit 20B may be a wiping member that is member impregnated with a liquid having a bactericidal action such as alcohol or a hypochlorous acid solution and wipes the inner wall surface 12A. The second sterilization unit 20B may have a configuration in which a plurality of types of sterilization members different from each other are arranged. A configuration in which sterilization is performed by using ultraviolet rays emitted by a phosphor (FIG. 12) that absorbs X-rays may be used. Since directions of fluorescence emission are isotropic (360-degree omnidirectional), in a case of using a configuration in which light is emitted from both upper and lower surfaces of the inner wall surface of the opening portion of the gantry 11, the inner wall of the gantry 11 can be sterilized, and the upper part of the inner wall surface (to which a virus is more likely to adhere) can also be sterilized at the same time as sterilization of the examination table 16.

Second Embodiment

Figure 17A:
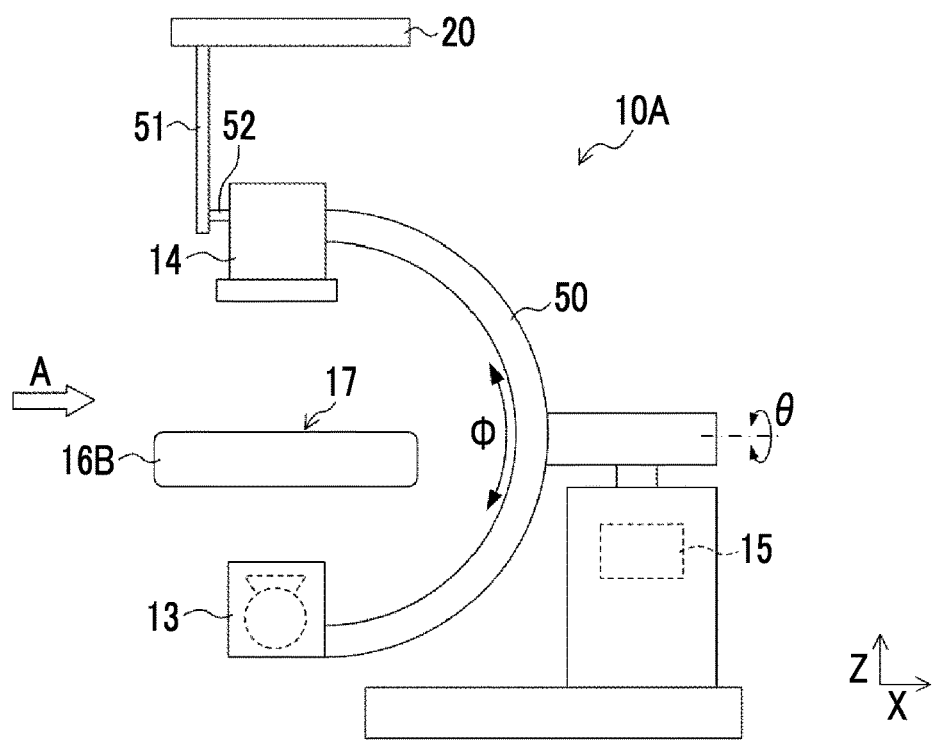
FIG. 17A is a diagram showing an example of a configuration of a radiography apparatus 10A that is an example of a medical apparatus according to an embodiment of the disclosed technology.
Figure 17B:
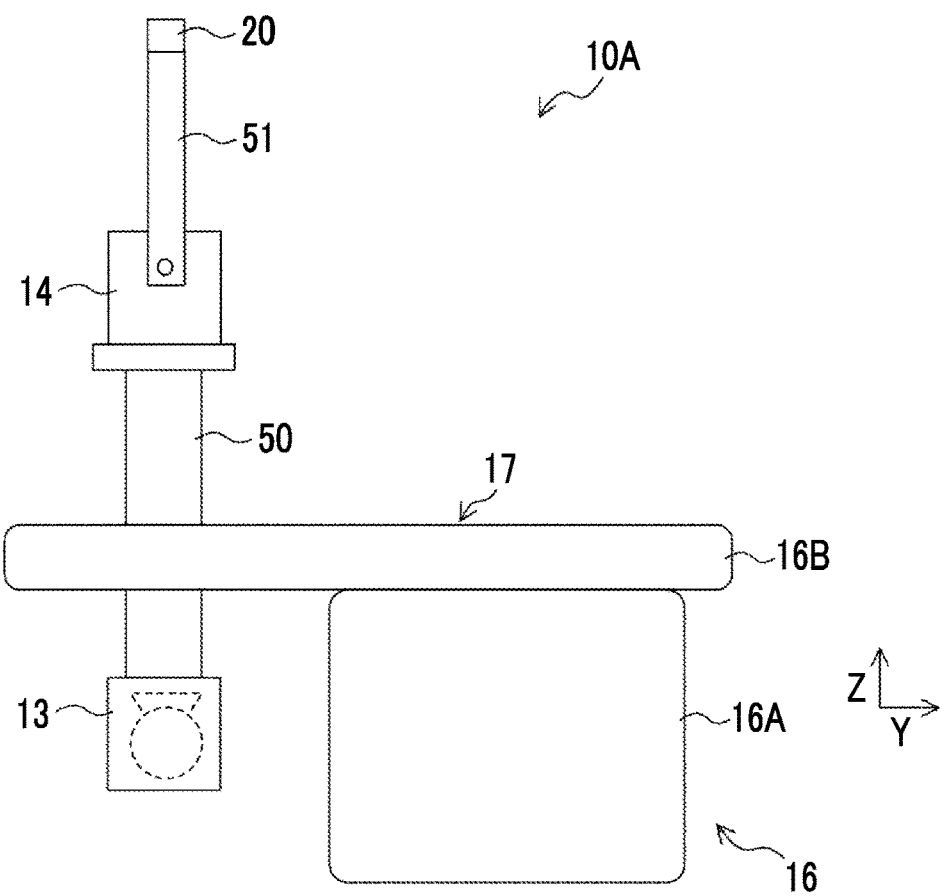
FIG. 17B is a view of the radiography apparatus according to the embodiment of the disclosed technology as viewed from a direction of an arrow A in FIG. 17A.

FIG. 17A is a diagram (X-Z plan view) showing an example of a configuration of a radiography apparatus 10A that is an example of a medical apparatus according to a second embodiment of the disclosed technology. FIG. 17B is a view (Y-Z plan view) of the radiography apparatus 10A viewed from a direction of an arrow A in FIG. 17A. In the following description, a vertical direction will be referred to as a Z direction, a slide direction of the bed portion 16B will be referred to as a Y direction, and a direction perpendicular to both the Z direction and the Y direction will be referred to as an X direction.

The radiography apparatus 10A has a so-called C-arm type form, and includes a radiation source unit 13 attached to one end of a C-arm 50 and a detection unit 14 attached to the other end of the C-arm 50. The radiography apparatus 10A further includes a control unit 15 and an examination table 16. The C-arm 50 is rotatable in a 0 direction and a 1 direction shown in FIG. 17A, and is further liftable and lowerable in the Z direction. The radiation source unit 13 and the detection unit 14 can be each rotated and lifted and lowered in accordance with rotation and movement of the C-arm 50 while maintaining a positional relationship of facing each other. In the radiography apparatus 10A according to the present embodiment, the detection unit 14 is disposed above a bed portion 16B, and the radiation source unit 13 is disposed below the bed portion 16B.

The examination table 16 has a base portion 16A fixed to a floor and a bed portion 16B on which a subject (examinee) lies. A surface of the bed portion 16B is a contact surface 17 with which the subject (examinee) comes into contact. The bed portion 16B is installed to protrude into a region between the radiation source unit 13 and the detection unit 14 attached to the C-arm 50. In a case of capturing a radiation image, by sliding the bed portion 16B, it is possible to cause any part of a subject (examinee) to be included in an imaging visual field.

The examination table 16 is an example of a "table portion" in the disclosed technology. The "table portion" has a contact surface with which a subject comes into contact. Each constituent of the structure including the C-arm 50, the radiation source unit 13, and the detection unit 14 is an example of a "structural portion" in the disclosed technology, and is also an example of an "examination unit". The "structural portion" is defined as a relative position with respect to the "table portion" within a predetermined range. The "examination unit" examines a subject in a non-contact manner.

A sterilization unit 20 that sterilizes the contact surface 17 of the bed portion 16B is attached to the detection unit 14 via an arm portion 51. The sterilization unit 20 has an elongated rod-like shape, and one end of the sterilization unit 20 in the longitudinal direction is connected to one end of the arm portion 51. A rotation shaft 52 having the X direction as an axial direction is provided at the other end of the arm portion 51, and the arm portion 51 is rotatable about an axis of the rotation shaft 52. Similar to the first embodiment, as the sterilization unit 20, a sterilization unit that emit light having a bactericidal action, a sterilization unit that ejects a gas or a liquid having a bactericidal action, a sterilization unit including a wiping member, and a sterilization unit having a configuration in which a plurality of types of different sterilization members are arranged may be employed.

Figure 18A:
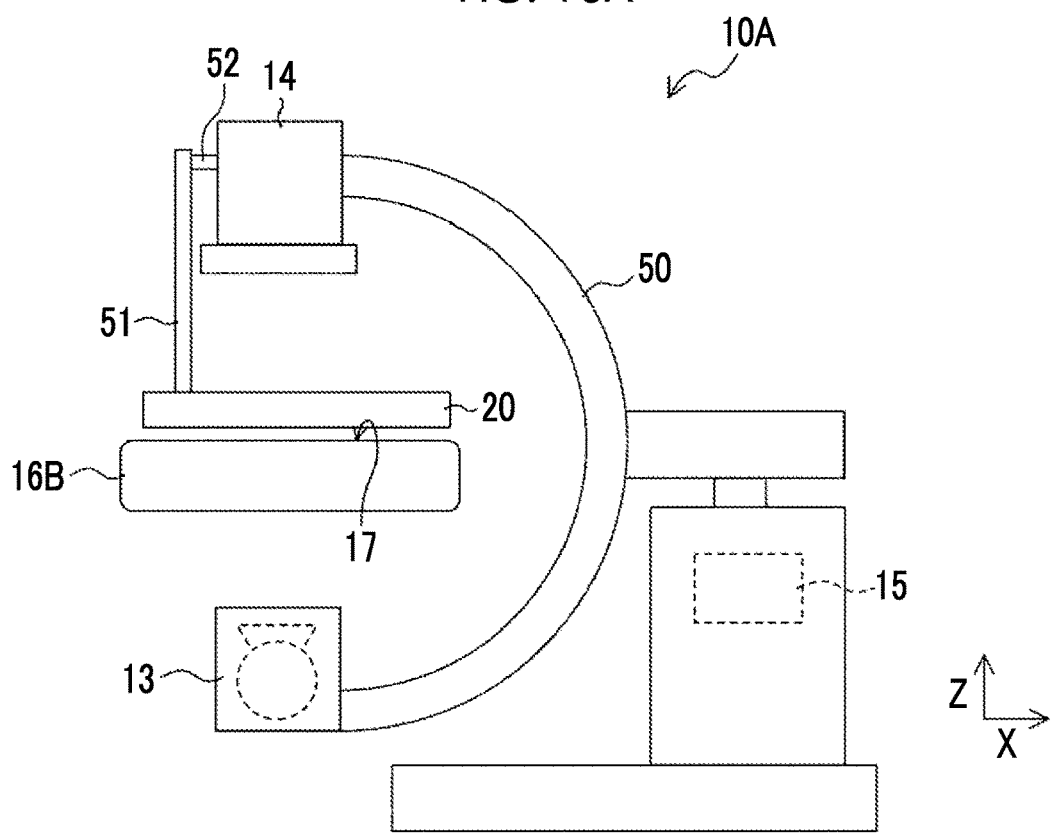
FIG. 18A is a plan view corresponding to FIG. 17A, showing a state of the sterilization unit in a case where a contact surface is sterilized.
Figure 18B:
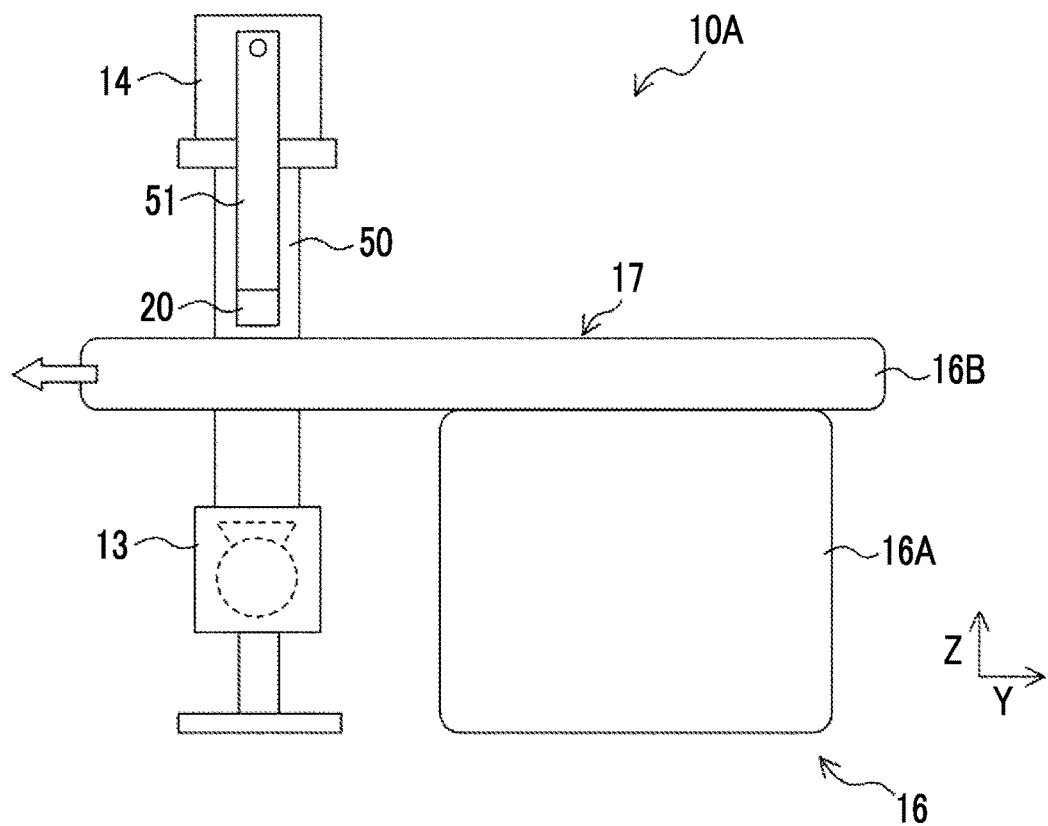
FIG. 18B is a plan view corresponding to FIG. 17B, showing a state of the sterilization unit in a case where the contact surface is sterilized.

FIGS. 18A and 18B are diagrams showing a state of the sterilization unit 20 in a case where the contact surface 17 is sterilized, and are plan views corresponding to FIGS. 17A and 17B, respectively. In a case where the contact surface 17 is sterilized, the sterilization unit 20 is brought into a first state of being brought into contact with or close to the contact surface 17 (a state in which a sterilization process can be performed). That is, as shown in FIGS. 18A and 18B, the arm portion 51 is positioned such that the sterilization unit 20 is located between the detection unit 14 and the bed portion 16B. As shown in FIG. 18B, by sliding the bed portion 16B while setting a state of the sterilization unit 20 to the first state, it is possible to sterilize the entire contact surface 17. A distance between the sterilization unit 20 and the contact surface 17 may be adjusted by adjusting a height position of the C-arm 50. In a case where the bed portion 16B is liftable and lowerable in the Z direction, a distance between the sterilization unit 20 and the contact surface 17 may be adjusted by adjusting a height position of the bed portion 16B.

On the other hand, in a case where a radiation image is captured by the radiography apparatus 10A, that is, in the normal use of the radiography apparatus 10A, the sterilization unit 20 is brought into the second state (retracted state) of being separated from the contact surface 17. Consequently, as shown in FIGS. 17A and 17B, the arm portion 51 is positioned such that the sterilization unit 20 is located above the detection unit 14.

According to the radiography apparatus 10A of the second embodiment of the disclosed technology, in the same manner as in the first embodiment, the contact surface 17 can be effectively sterilized without hindering the normal use of the radiography apparatus 10A.

In the above description, the case where the detection unit 14 is disposed above the bed portion 16B and the radiation source unit 13 is disposed below the bed portion 16B has been described as an example. However, the radiation source unit 13 may be disposed above the bed portion 16B, and the detection unit 14 may be disposed below the bed portion 16B. In this case, the sterilization unit 20 is attached to the radiation source unit 13 disposed above the bed portion 16B via the arm portion. In the radiography apparatus 10A, the sterilization units 20 in the forms shown in FIGS. 9A to 9C, FIGS. 10A to 10D, and FIG. 11 may be employed.

Third Embodiment

Figure 19:
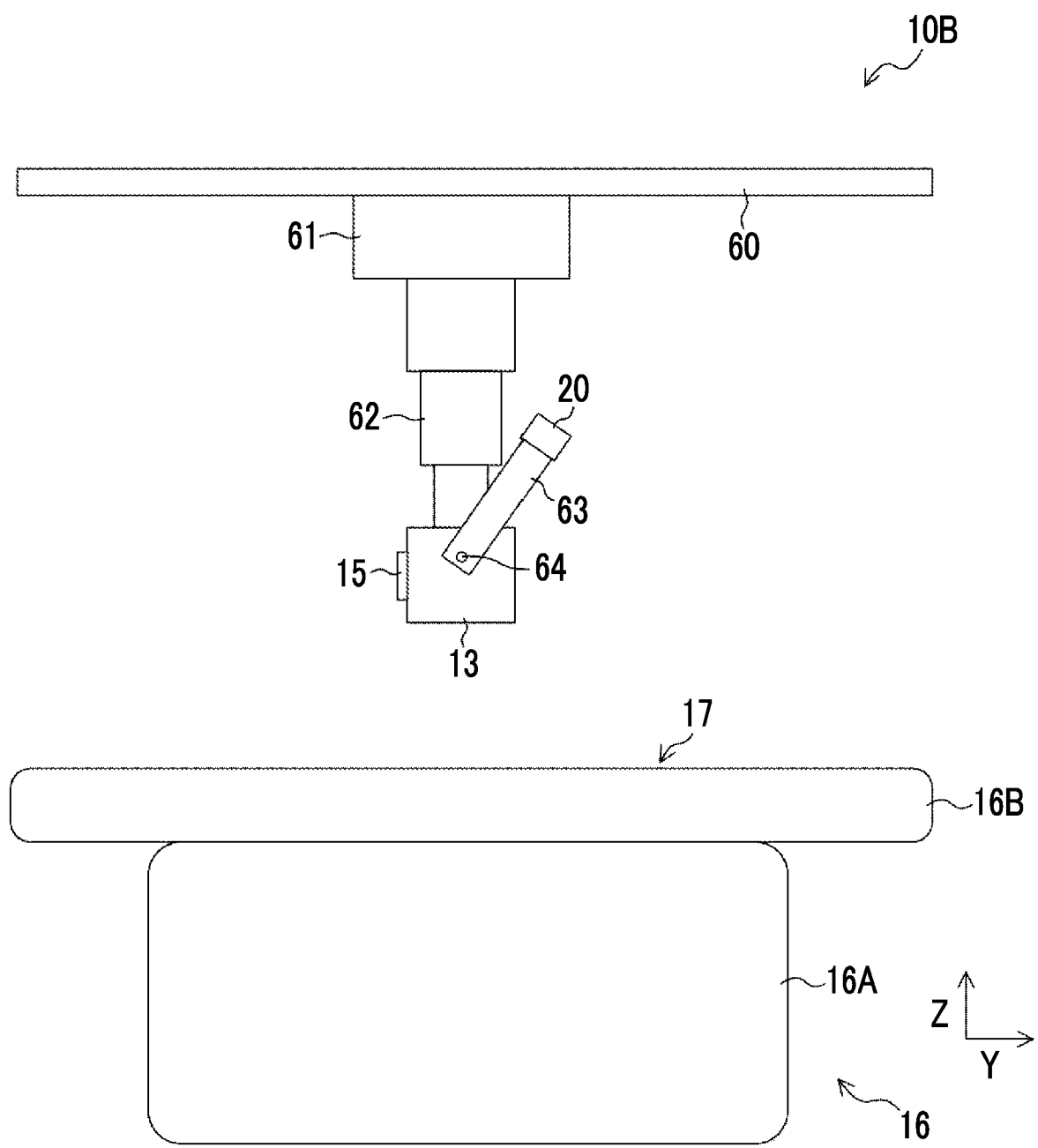
FIG. 19 is a diagram showing an example of a configuration of a radiography apparatus that is an example of a medical apparatus according to an embodiment of the disclosed technology.

FIG. 19 is a diagram (Y-Z plan view) showing an example of a configuration of a radiography apparatus 10B that is an example of a medical apparatus according to a third embodiment of the disclosed technology. In the following description, the vertical direction will be referred to as a Z direction, a travel direction of a travel portion 61 will be referred to as a Y direction, and a direction perpendicular to both the Z direction and the Y direction will be referred to as an X direction.

The radiography apparatus 10B has a so-called ceiling travel type form, and has a guide rail 60 attached to a ceiling, a travel portion 61 traveling on the guide rail 60, a strut portion 62 that is extendable and contractible and is connected to the travel portion 61, and a radiation source unit 13 attached to a tip end of the strut portion 62. The radiography apparatus 10B further includes a control unit 15 and an examination table 16.

The examination table 16 has a base portion 16A fixed to a floor and a bed portion 16B on which a subject (examinee) lies. A surface of the bed portion 16B is a contact surface 17 with which the subject (examinee) comes into contact. The examination table 16 is installed to be located below the radiation source unit 13. In a case where the travel portion 61 is traveling on the guide rail 60, the radiation source unit 13 can be positioned, and any part of a subject (examinee) can be included in an imaging visual field. As a detection unit (not shown) for detecting radiation, a portable detection unit may be used. The detection unit may be built into the bed portion 16B.

The examination table 16 is an example of a "table portion" in the disclosed technology. The "table portion" has a contact surface with which a subject comes into contact. Each constituent of the structure including the guide rail 60, the travel portion 61, the strut portion 62, and the radiation source unit 13 is an example of a "structural portion" in the disclosed technology, and is also an example of an "examination unit". The "structural portion" is defined as a relative position with respect to the "table portion" within a predetermined range. The "examination unit" examines a subject in a non-contact manner.

A sterilization unit 20 that sterilizes the contact surface 17 of the bed portion 16B is attached to the radiation source unit 13 via an arm portion 63. The sterilization unit 20 has an elongated rod-like shape, and one end of the sterilization unit 20 in the longitudinal direction is connected to one end of the arm portion 63. A rotation shaft 64 having the X direction as an axial direction is provided at the other end of the arm portion 63, and the arm portion 63 is rotatable about an axis of the rotation shaft 64. The sterilization unit 20 is movable in the Y direction in a case where the travel portion 61 is travelling on the guide rail 60. Similar to the first embodiment, as the sterilization unit 20, a sterilization unit that emit light having a bactericidal action, a sterilization unit that ejects a gas or a liquid having a bactericidal action, a sterilization unit including a wiping member, and a sterilization unit having a configuration in which a plurality of types of different sterilization members are arranged may be employed.

Figure 20A:
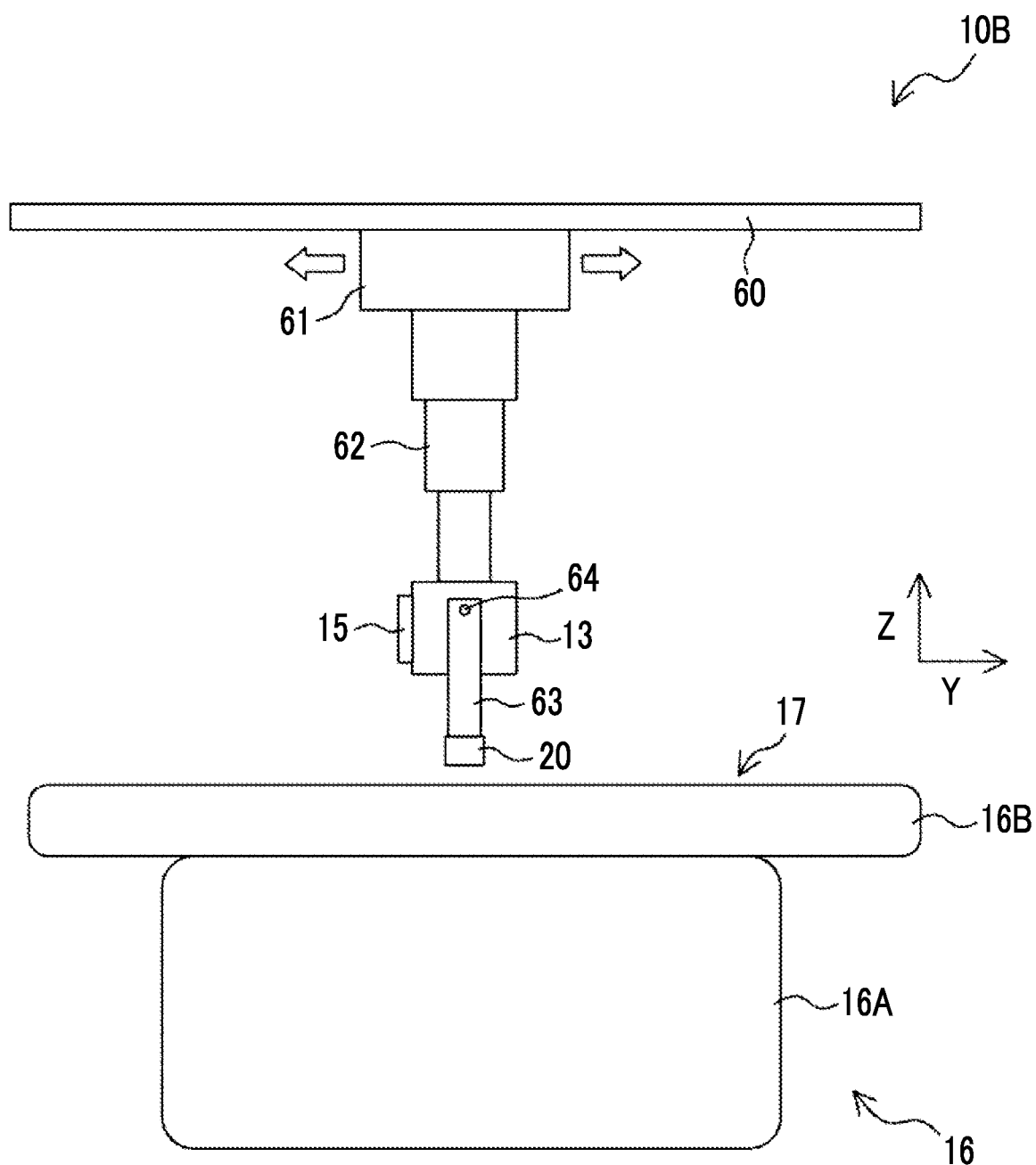
FIG. 20A is a diagram showing a state of the sterilization unit in a case where a contact surface is sterilized in the radiography apparatus according to the embodiment of the disclosed technology.
Figure 20B:
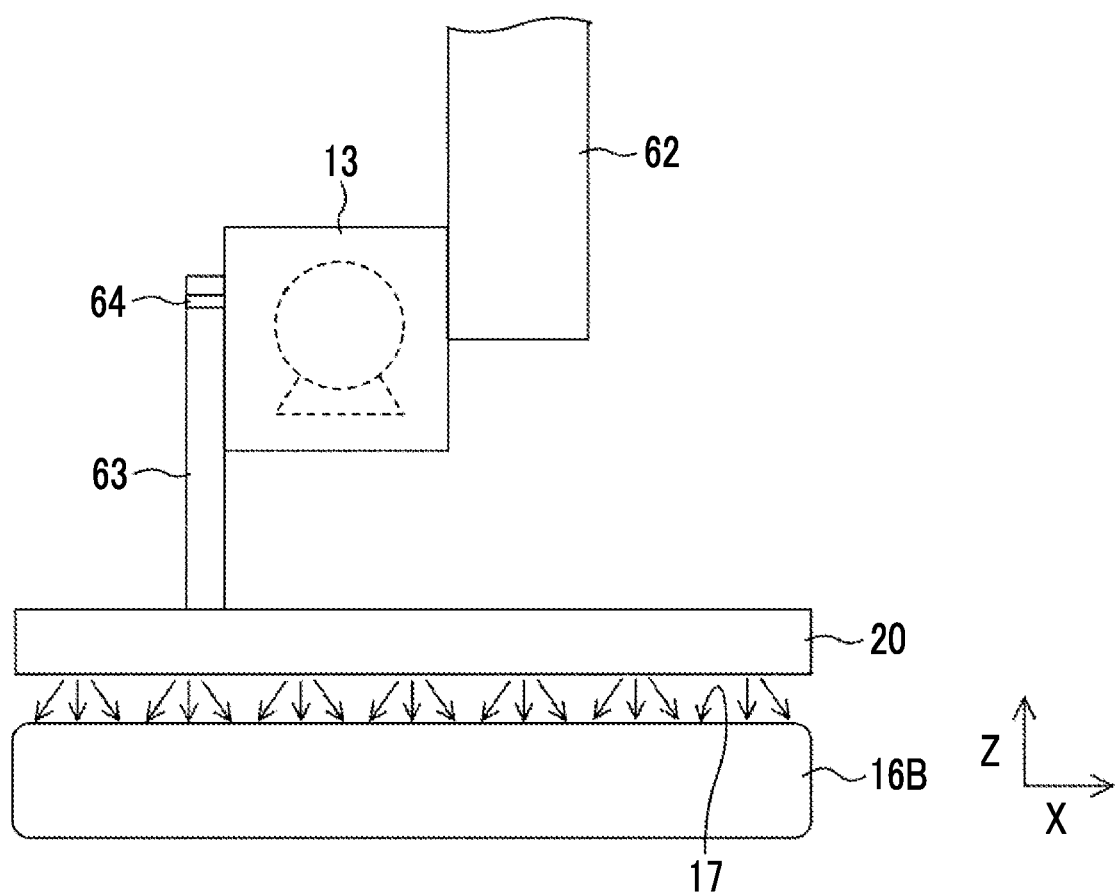
FIG. 20B is a diagram showing a state of the sterilization unit in a case where the contact surface is sterilized in the radiography apparatus according to the embodiment of the disclosed technology.

FIGS. 20A and 20B each are diagrams showing a state of the sterilization unit 20 in a case where the contact surface 17 is sterilized. FIG. 20A is a Y-Z plan view, and FIG. 20B is an X-Z plan view showing the enlarged sterilization unit 20. In a case where the contact surface 17 is sterilized, the sterilization unit 20 is brought into the first state of being in contact with or close to the contact surface 17 (a state in which the sterilization process can be performed). That is, as shown in FIGS. 20A and 20B, the arm portion 63 is positioned such that the sterilization unit 20 is located between the radiation source unit 13 and the bed portion 16B. The entire contact surface 17 can be sterilized by causing the travel portion 61 to travel to move the sterilization unit 20 in the Y direction while setting the sterilization unit 20 to the first state. A distance between the sterilization unit 20 and the contact surface 17 can be adjusted by adjusting a length of the strut portion 62 that is extendable and contractible. In a case where the bed portion 16B is liftable and lowerable in the Z direction, a distance between the sterilization unit 20 and the contact surface 17 may be adjusted by adjusting a height position of the bed portion 16B.

On the other hand, in a case where a radiation image is captured by the radiography apparatus 10B, that is, in the normal use of the radiography apparatus 10B, the sterilization unit 20 is brought into the second state (retracted state) of being separated from the contact surface 17. That is, as shown in FIG. 19, the arm portion 63 is positioned such that the sterilization unit 20 is located above the radiation source unit 13.

According to the radiography apparatus 10B of the third embodiment of the disclosed technology, in the same manner as in the first embodiment, the contact surface 17 can be effectively sterilized without hindering the normal use of the radiography apparatus 10B. In the radiography apparatus 10B, the sterilization units 20 in the forms shown in FIGS. 9A to 9C, FIGS. 10A to 10D, and FIG. 11 may be employed.

Fourth Embodiment

Figure 21A:
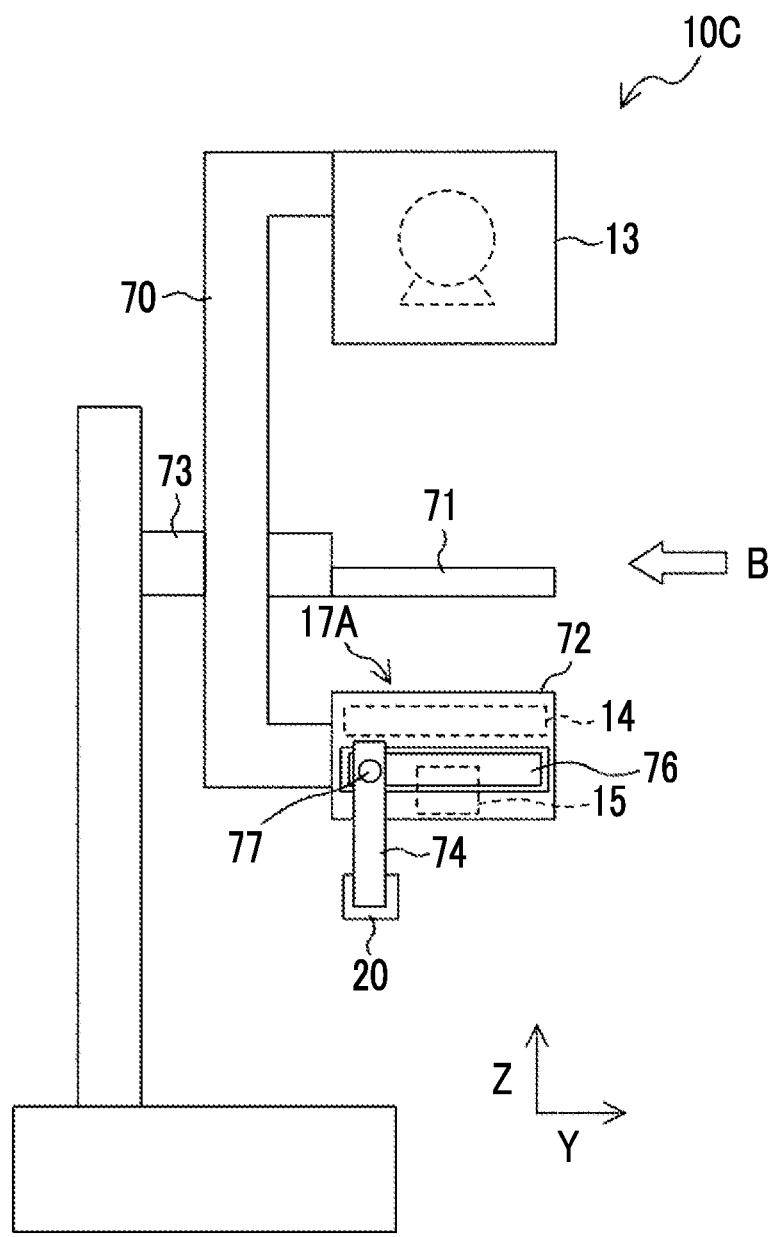
FIG. 21A is a diagram showing an example of a configuration of a mammography apparatus that is an example of a medical apparatus according to an embodiment of the disclosed technology.
Figure 21B:
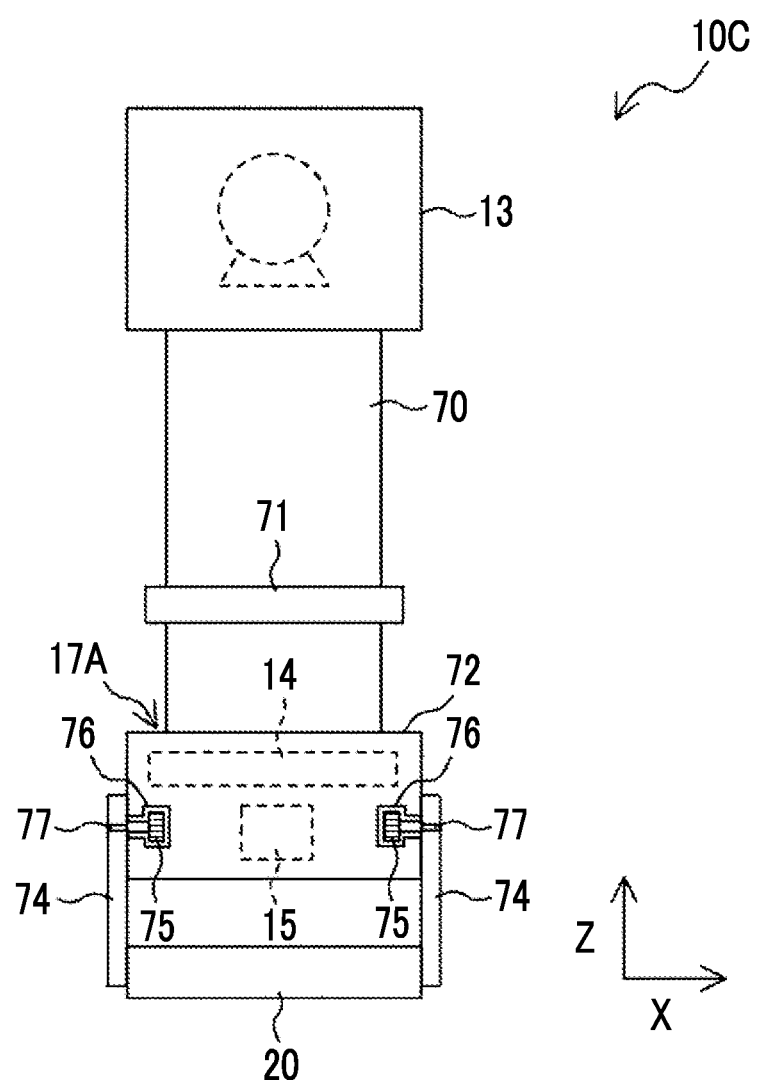
FIG. 21B is a view of the mammography apparatus according to the embodiment of the disclosed technology as viewed from a direction of an arrow B in FIG. 21A.

FIG. 21A is a diagram (Y-Z plan view) showing an example of a configuration of a mammography apparatus 10C that is an example of a medical apparatus according to a fourth embodiment of the disclosed technology. FIG. 21B is a view (X-Z plan view) of the mammography apparatus 10C as viewed from a direction of an arrow B in FIG. 21A. In the following description, a vertical direction will be referred to as a Z direction, and a direction in which an examinee of which a radiation image is captured by the mammography apparatus 10C faces at the time of imaging will be referred to as a Y direction, and a direction perpendicular to both the Z direction and the Y direction will be referred to as an X direction.

The mammography apparatus 10C includes an arm portion 70, a radiation source unit 13, a detection unit 14, a compression plate 71, an imaging table 72, and a control unit 15. The radiation source unit 13 and the imaging table 72 are attached to the arm portion 70, and the detection unit 14 and the control unit 15 are provided inside the imaging table 72.

The arm portion 70 that is connected to a rotation shaft 73 having the Y direction as an axial direction is rotatable about an axis of the rotation shaft 73, and is further liftable and lowerable in the Z direction. The radiation source unit 13 and the detection unit 14 can be each rotated and lifted and lowered in accordance with rotation and movement of the arm portion 70 while maintaining a positional relationship of facing each other. The compression plate 71 is provided to be liftable and lowerable in the Z direction between the radiation source unit 13 and the imaging table 72. In a case of capturing a radiation image of a breast that is a subject, the breast is sandwiched between the compression plate 71 and the imaging table 72 and is compressed. A surface of the imaging table 72 is a contact surface 17A with which the breast that is a subject comes into contact.

The imaging table 72 is an example of a "table portion" in the disclosed technology. The "table portion" has a contact surface with which a subject comes into contact. The radiation source unit 13 is an example of a "structural portion" in the disclosed technology, and is also an example of an "examination unit". The "structural portion" is defined as a relative position with respect to the "table portion"

within a predetermined range. The "examination unit" examines a subject in a non-contact manner. The compression plate 71 is an example of a "fixing unit" in the disclosed technology. The "fixing unit" fixes a subject by sandwiching the subject between the "fixing unit" and the "table portion".

A sterilization unit 20 that sterilizes the contact surface 17A of the imaging table 72 is attached to the imaging table 72 via an arm portion 74. The sterilization unit 20 is attached to the imaging table 72 via a pair of arm portions 74 attached to both ends thereof in the longitudinal direction. A roller 75 is provided at one end of the arm portion 74 in the longitudinal direction. The roller 75 is fitted in a guide groove 76 provided on the side surface of the imaging table 72 in the Y direction. The roller 75 is driven by a motor (not shown), and thus the arm portion 74 can be moved together with the sterilization unit 20 in the Y direction. The arm portion 74 is rotatable about an axis of a rotation shaft 77 having the X direction as an axial direction and provided at the same position as the attachment position of the roller 75. Similar to the first embodiment, as the sterilization unit 20, a sterilization unit that emit light having a bactericidal action, a sterilization unit that ejects a gas or a liquid having a bactericidal action, a sterilization unit including a wiping member, and a sterilization unit having a configuration in which a plurality of types of different sterilization members are arranged may be employed.

Figure 22A:
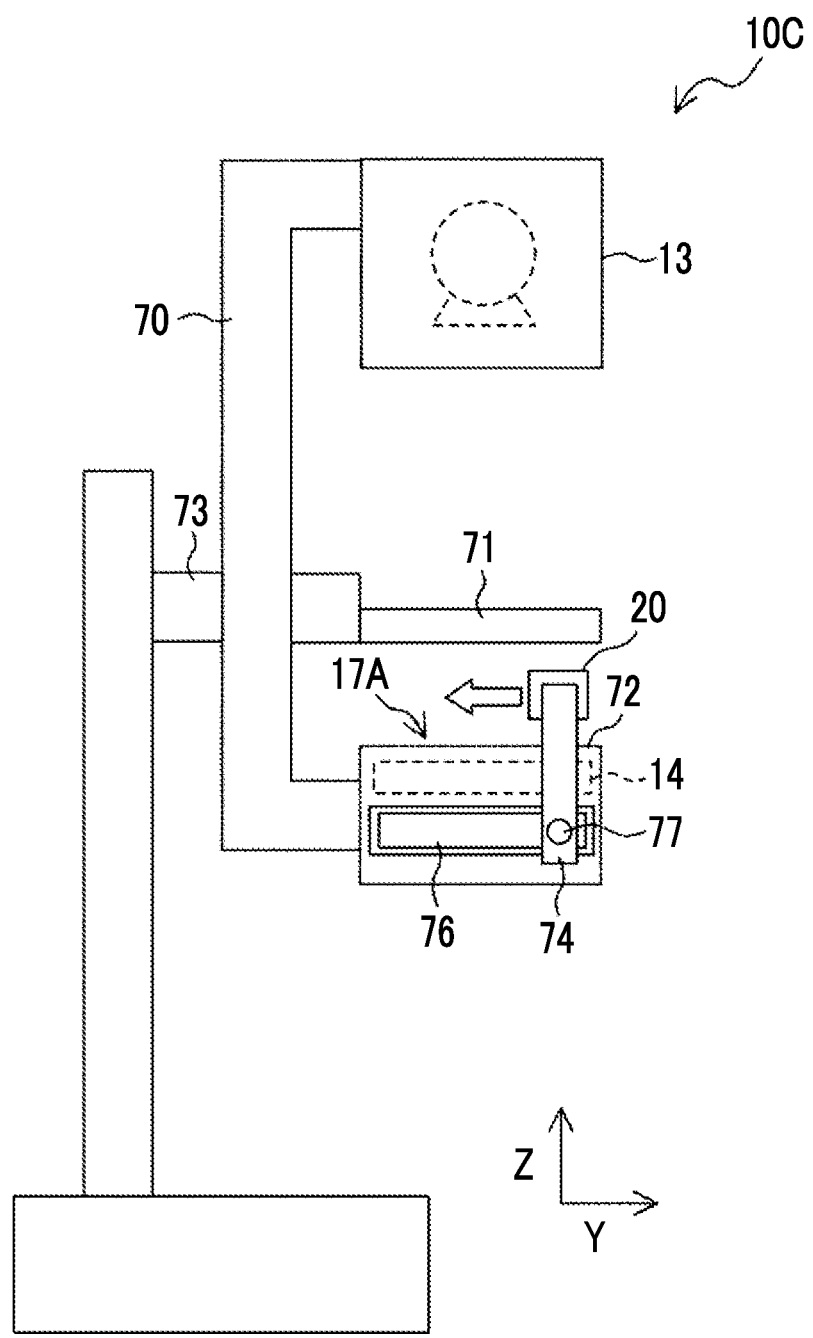
FIG. 22A is a plan view corresponding to FIG. 21A, showing a state of the sterilization unit in a case where the contact surface is sterilized.
Figure 22B:
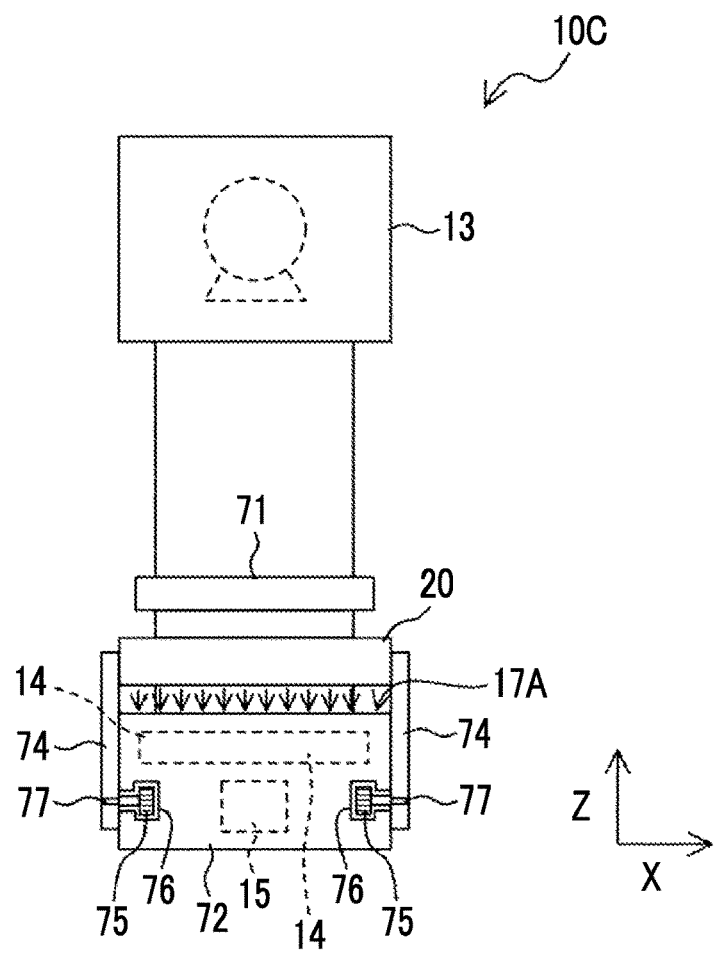
FIG. 22B is a plan view corresponding to FIG. 21B showing a state of the sterilization unit in a case where the contact surface is sterilized.

FIGS. 22A and 22B are diagrams showing a state of the sterilization unit 20 in a case where the contact surface 17A is sterilized, and are plan views corresponding to FIGS. 21A and 21B, respectively. In a case where the contact surface 17A is sterilized, the sterilization unit 20 is brought into the first state of being in contact with or close to the contact surface 17A (a state in which the sterilization process can be performed). That is, as shown in FIGS. 22A and 22B, the arm portion 74 is positioned such that the sterilization unit 20 is located above the imaging table 72. By driving the roller 75 while setting a state of the sterilization unit 20 to the first state, the arm portion 74 is moved together with the sterilization unit 20 in the extension direction (Y direction) of the guide groove 76. Consequently, it is possible to sterilize the entire contact surface 17A.

On the other hand, in a case where a radiation image is captured by the mammography apparatus 10C, that is, in the normal use of the mammography apparatus 10C, the sterilization unit 20 is brought into the second state (retracted state) of being separated from the contact surface 17A. That is, as shown in FIG. 21A, the arm portion 74 is positioned such that the sterilization unit 20 is located below the imaging table 72 at a terminal position on the side opposite to a chest wall of an examinee.

According to the mammography apparatus 10C of the fourth embodiment of the disclosed technology, in the same manner as in the first embodiment, it is possible to effectively sterilize the contact surface 17A without hindering the normal use of the mammography apparatus 10C.

Figure 23:
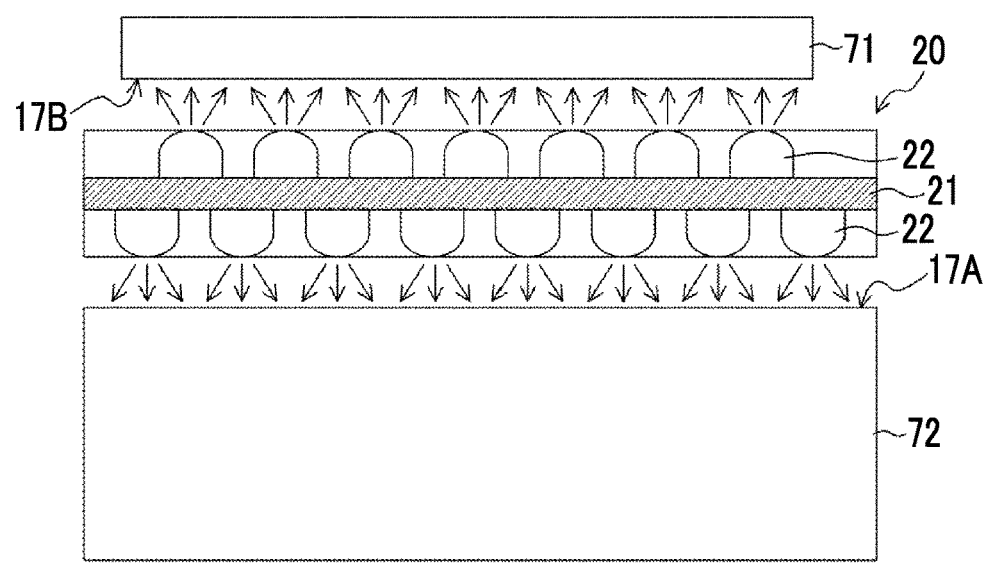
FIG. 23 is a diagram showing an example of a configuration of the sterilization unit according to the embodiment of the disclosed technology.

FIG. 23 is a diagram showing an example of a configuration of the sterilization unit 20 capable of simultaneously sterilizing both the contact surface 17A of the imaging table 72 with a breast and the contact surface 17B of the compression plate 71 with the breast. As shown in FIG. 23, the sterilization unit 20 may include a plurality of light sources 22 having a bactericidal action and emitting light, which are arranged on both surfaces of a wiring board 21. An optical axis direction of the light sources 22 arranged on each surface of the wiring board 21 is the Z direction. That is, the sterilization unit 20 can emit light having a bactericidal action toward both the upper side and the lower side in the Z direction. In a case where the contact surfaces 17A and 17B are sterilized, a state occurs in which one surface of the sterilization unit 20 faces the contact surface 17A of the imaging table 72 with a breast, and the other surface of the sterilization unit 20 faces the contact surface 17B of the compression plate 71 with the breast, and light from the light sources 22 is applied to both the contact surfaces 17A and 17B. In a case where the compression plate 71 is sterilized, it is preferable to control a height position of the compression plate 71 such that the compression plate 71 comes close to or into contact with the sterilization unit 20.

Figure 24A:
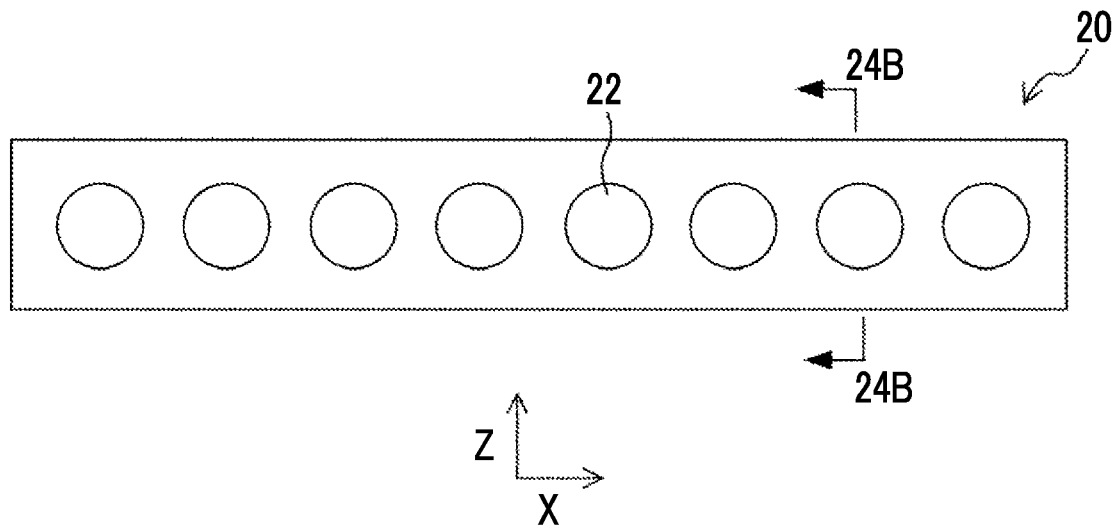
FIG. 24A is a diagram showing an example of a configuration of the sterilization unit according to the embodiment of the disclosed technology.
Figure 24B:
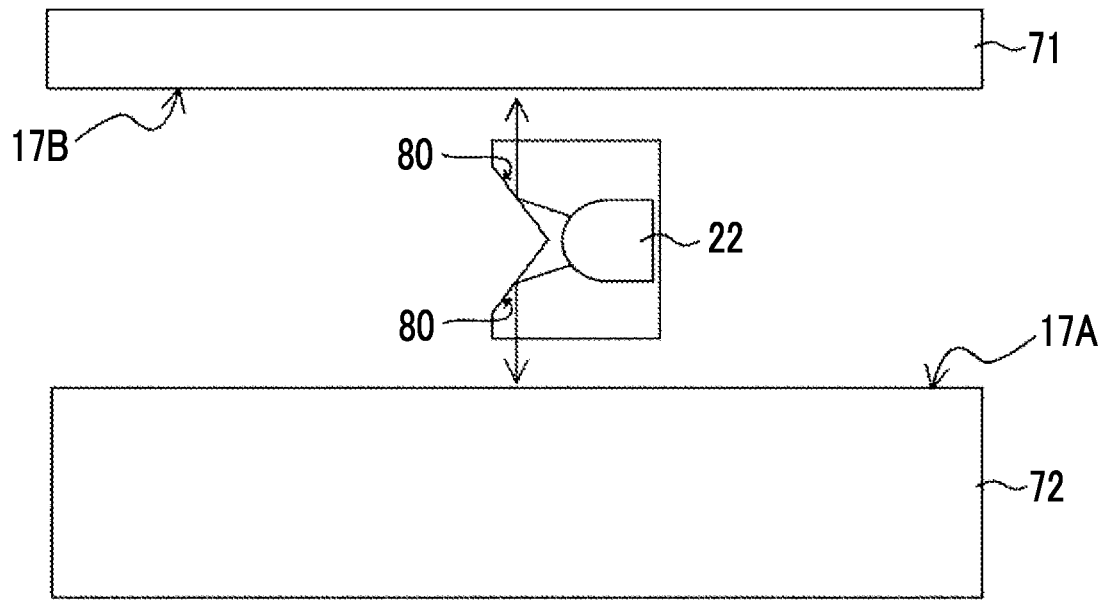
FIG. 24B is a sectional view taken along the line 24B-24B in FIG. 24A.

FIG. 24A is a diagram showing another example of a configuration of the sterilization unit 20 capable of simultaneously sterilizing both the contact surface 17A of the imaging table 72 with a breast and the contact surface 17B of the compression plate 71 with the breast. FIG. 24B is a sectional view taken along the line 24B-24B in FIG. 24A. As shown in FIG. 24B, the sterilization unit 20 may include a plurality of light sources 22 that are arranged in the X direction and emit light having a bactericidal action, and a reflecting surface 80 that reflects light from the light source 22 to the upper side and the lower side in the Z direction. An optical axis direction of the light source 22 is the Y direction. The sterilization unit 20 may be configured to eject a liquid or a gas having a bactericidal action toward both the upper side and the lower side in the Z direction. The sterilization unit 20 may include wiping members that wipe the contact surfaces 17A and 17B on both one surface facing the contact surface 17A of the imaging table 72 with the breast and the other surface facing the contact surface 17B of the compression plate 71 with the breast.

The disclosed technology can be applied to medical apparatuses other than those exemplified in the first to fourth embodiments described above. For example, the disclosed technology can be applied to a radiography apparatus of a type that captures a radiation image in an upright position, a radiography apparatus that performs fluoroscopic imaging, a magnetic resonance imaging (MRI) apparatus, a positron emission tomography (PET), a bone mineral quantification apparatus, and a radiotherapy apparatus. That is, the disclosed technology can be applied to any medical apparatus including a table portion having a contact surface with which a subject comes into contact and a structural portion in which a relative position with the table portion is determined within a predetermined range. For example, in a case where a subject comes into contact with a detector that detects radiation, such as a radiography apparatus of a type that captures a radiation image in an upright position, the detector is considered as a "table portion having a contact surface" and is a target of a sterilization process.

The disclosure of Japanese Patent Application No. 2020-180888 filed on Oct. 28, 2020 is incorporated herein by reference in its entirety. All the documents, the patent applications, and the technical standards disclosed in the present specification are incorporated by reference in the present specification to the same extent as in a case where the individual documents, patent applications, and technical standards are specifically and individually stated to be incorporated by reference.

What is claimed is:
1. A medical apparatus comprising:
a table portion that has a contact surface with which a subject comes into contact;
a structural portion in which a relative position with the table portion is determined within a predetermined range; and a sterilization unit that is attached to the table portion or the structural portion and sterilizes the contact surface, wherein the sterilization unit is configured to switch between a first state in which the sterilization unit is in contact with or close to the contact surface and a second state in which the sterilization unit is separated from the contact surface, and wherein the structural portion is an examination unit that examines the subject in a non-contact manner.

2. The medical apparatus according to claim 1, wherein, in the first state, a distance between the sterilization unit and the contact surface is 10 cm or less.

3. The medical apparatus according to according to claim 1, wherein the sterilization unit includes a light source that emits ultraviolet rays.

4. The medical apparatus according to claim 1, further comprising:

a radiation source unit that emits radiation, wherein the sterilization unit includes a phosphor that absorbs radiation and emits ultraviolet rays, and in the first state, the radiation radiated from the radiation source unit is applied to the phosphor.

5. The medical apparatus according to claim 1, wherein the sterilization unit ejects a liquid or a gas having a bactericidal action toward the contact surface.

6. The medical apparatus according to claim 1, wherein the sterilization unit includes a wiping member that is a member impregnated with a liquid having a bactericidal action and wipes the contact surface.

7. The medical apparatus according to claim 1, further comprising:

a fixing unit that fixes the subject by sandwiching the subject between the table portion and the fixing unit, wherein the sterilization unit is configured to emit at least one of light, a liquid, or a gas having a bactericidal action from both a first surface and a second surface opposite to the first surface, and in the first state, the first surface faces the contact surface of the table portion and the second surface faces a surface of the fixing unit that comes into contact with the subject.

8. The medical apparatus according to claim 1, further comprising:

a control unit that controls a sterilization process of sterilizing the contact surface with the sterilization unit, wherein at least one of the sterilization unit or the contact surface is movable in a surface direction of the contact surface, and in the sterilization process, the control unit sets a state of the sterilization unit to the first state, and moves at least one of the sterilization unit or the contact surface in the surface direction.

9. The medical apparatus according to claim 8, further comprising:

a region detection unit that detects a contact region of the contact surface with which the subject comes into contact, wherein, in the sterilization process, the control unit sterilizes the contact surface by setting a sterilization intensity in the contact region detected by the region detection unit to be higher than a sterilization intensity in a region other than the contact region.

10. The medical apparatus according to claim 8, further comprising:

a height detection unit that detects a height of the contact surface, wherein, in the sterilization process, the control unit controls a height of the sterilization unit in accordance with a change in the height of the contact surface detected by the height detection unit such that a distance between the sterilization unit and the contact surface is constant.

11. The medical apparatus according to claim 8, wherein the control unit starts the sterilization process on the basis of order information regarding diagnosis or treatment of the subject.

12. The medical apparatus according to claim 8, wherein, in the sterilization process, the control unit sterilizes the contact surface in a sterilization mode selected from a plurality of sterilization modes in which sterilization intensities are different from each other.

13. The medical apparatus according to claim 1, wherein the table portion is an examination table on which an examinee to be treated in the medical apparatus lies.

14. A medical apparatus, comprising:

a table portion that has a contact surface with which a subject comes into contact;

a structural portion in which a relative position with the table portion is determined within a predetermined range; and a sterilization unit that is attached to the table portion or the structural portion and sterilizes the contact surface, wherein the sterilization unit is configured to switch between a first state in which the sterilization unit is in contact with or close to the contact surface and a second state in which the sterilization unit is separated from the contact surface, and wherein the structural portion is a radiation source unit that emits radiation.

15. A medical apparatus, comprising:

a table portion that has a contact surface with which a subject comes into contact;

a structural portion in which a relative position with the table portion is determined within a predetermined range; and a sterilization unit that is attached to the table portion or the structural portion and sterilizes the contact surface, wherein the sterilization unit is configured to switch between a first state in which the sterilization unit is in contact with or close to the contact surface and a second state in which the sterilization unit is separated from the contact surface, and wherein the structural portion is a detection unit that detects radiation.

* * * * *